United States Patent
Green et al.

(10) Patent No.: US 6,569,120 B1
(45) Date of Patent: *May 27, 2003

(54) SEAL ASSEMBLY

(75) Inventors: David T. Green, Westport, CT (US); Henry Bolanos, East Norwalk, CT (US); Salvatore Castro, Seymour, CT (US); Henry Sienkiewicz, Stamford, CT (US); Stephan A. DeFonzo, Bridgeport, CT (US); Douglas J. Cuny, Bethel, CT (US); Wayne P. Young, Brewster, NY (US)

(73) Assignee: United States Surgical Corporation, Norwalk, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/814,757

(22) Filed: Mar. 7, 1997

Related U.S. Application Data

(63) Continuation of application No. 08/378,989, filed on Jan. 24, 1995, now abandoned, which is a continuation of application No. 07/950,205, filed on Sep. 23, 1992, now abandoned, which is a continuation-in-part of application No. 07/873,416, filed on Apr. 24, 1992, now abandoned, and application No. 07/781,063, filed on Oct. 18, 1991, now Pat. No. 5,203,773.

(51) Int. Cl.[7] .................. A61M 5/178; F16K 15/14; F16K 15/16

(52) U.S. Cl. ................. 604/167.04; 604/167.07; 137/849; 137/855

(58) Field of Search ............... 604/93, 164, 167, 604/244, 246–247, 256, 905, 167.04, 167.06; 137/849, 855; 251/149.1

(56) References Cited

U.S. PATENT DOCUMENTS

| 729,423 | A | 5/1903 | Scheiber et al. |
|---|---|---|---|
| 2,699,826 | A | 1/1955 | Emerson |
| 2,797,837 | A | 7/1957 | Roberts |
| 3,086,797 | A | 4/1963 | Webb |
| 3,197,173 | A | 7/1965 | Taubenheim |
| 3,438,607 | A | 4/1969 | Williams et al. |
| 3,766,916 | A | 10/1973 | Moorehead et al. |
| 3,811,440 | A | 5/1974 | Moorehead et al. |
| 3,856,010 | A | 12/1974 | Moorehead et al. |
| 3,875,938 | A | 4/1975 | Mellor |
| 3,920,215 | A | 11/1975 | Knauf |
| 3,970,089 | A | 7/1976 | Saice |
| 3,977,400 | A | 8/1976 | Moorehead |
| 3,994,287 | A | 11/1976 | Turp et al. |

(List continued on next page.)

FOREIGN PATENT DOCUMENTS

| DE | 3042229 | * 5/1982 | .............. 604/167 |
|---|---|---|---|
| EP | 0344907 | 12/1989 | |
| EP | 0350291 | 1/1990 | |
| GB | 2019219 | 10/1979 | |
| GB | 2065479 | 7/1981 | |

Primary Examiner—Dennis Ruhl
Assistant Examiner—K. M. Reichle

(57) ABSTRACT

A valve assembly is provided for permitting the introduction of a surgical instrument into a patient's body while providing a substantial seal about the instrument. The valve assembly includes a sealing gasket assembly providing a fluid tight seal before instrument insertion, and is configured and dimensioned for accommodating an instrument and providing a substantial fluid tight seal after insertion of an instrument. The valve assembly may further include a deformable sealing member having a substantially central aperture for accommodating the instrument. The sealing member provides a substantial seal about the instrument when the instrument is passed therethrough impeding the egress of fluids and gasses through the valve assembly.

14 Claims, 16 Drawing Sheets

U.S. PATENT DOCUMENTS

| | | |
|---|---|---|
| 4,000,739 A | 1/1977 | Stevens |
| 4,149,535 A | 4/1979 | Volder |
| 4,177,814 A | 12/1979 | Knepshield et al. |
| 4,231,400 A | 11/1980 | Friedling et al. |
| 4,240,411 A | 12/1980 | Hosono |
| 4,243,034 A | 1/1981 | Brandt |
| 4,324,239 A | 4/1982 | Gordon et al. |
| 4,378,013 A | 3/1983 | LeFevre |
| 4,424,833 A | 1/1984 | Spector et al. |
| 4,430,081 A | 2/1984 | Timmermans |
| 4,436,519 A | 3/1984 | O'Neill |
| 4,473,369 A | 9/1984 | Lueders et al. |
| 4,475,548 A | 10/1984 | Muto |
| 4,496,348 A | 1/1985 | Genese et al. |
| 4,580,573 A | 4/1986 | Quinn |
| 4,610,665 A | 9/1986 | Matsumoto et al. |
| 4,610,674 A | 9/1986 | Suzuki et al. |
| 4,626,245 A | 12/1986 | Weinstein |
| 4,634,421 A | 1/1987 | Hegemann |
| 4,634,432 A | 1/1987 | Kocak |
| 4,654,030 A | 3/1987 | Moll et al. |
| 4,655,752 A | 4/1987 | Honkanen et al. |
| 4,673,393 A | 6/1987 | Suzuki et al. |
| 4,723,550 A | 2/1988 | Bales et al. |
| 4,786,028 A | 11/1988 | Hammond |
| 4,798,594 A | 1/1989 | Hillstead |
| 4,817,631 A | 4/1989 | Schnepp-Pesch et al. |
| 4,839,471 A | 6/1989 | Clark et al. |
| 4,842,591 A | 6/1989 | Luther |
| 4,869,717 A | 9/1989 | Adair |
| 4,874,377 A | 10/1989 | Newgard et al. |
| 4,895,346 A | 1/1990 | Steigerwald |
| 4,895,565 A | 1/1990 | Hillstead |
| 4,909,798 A | 3/1990 | Fleischhacker et al. |
| 4,917,668 A | 4/1990 | Haindl |
| 4,929,235 A | 5/1990 | Merry et al. |
| 4,943,280 A | 7/1990 | Lander |
| 4,960,259 A | 10/1990 | Sunnanväder et al. |
| 4,960,412 A | 10/1990 | Fink |
| 4,978,341 A | 12/1990 | Niederhauser |
| 5,000,745 A | 3/1991 | Guest et al. |
| 5,009,391 A | 4/1991 | Steigerwald |
| 5,009,643 A | 4/1991 | Reich et al. |
| 5,041,095 A | 8/1991 | Littrell |
| 5,053,014 A | 10/1991 | Van Heugten |
| 5,053,016 A | 10/1991 | Lander |
| 5,098,393 A * | 3/1992 | Amplatz et al. ............. 604/167 |
| 5,104,389 A | 4/1992 | Shichman |
| 5,127,626 A | 7/1992 | Hilal et al. |
| 5,127,909 A | 7/1992 | Shichman |
| 5,167,636 A | 12/1992 | Clement |
| 5,176,653 A * | 1/1993 | Metals ....................... 604/167 |
| 5,180,365 A * | 1/1993 | Ensmingor et al. ......... 604/167 |
| 5,226,879 A * | 7/1993 | Ensmingor et al. ......... 604/256 |

\* cited by examiner

SEAL ASSEMBLY

CROSS REFERENCE TO RELATED APPLICATION

This is a continuation, of application Ser. No. 08/378,989 filed on Jan. 24, 1995 now abn., which is a continuation of application Ser. No. 07/950,205, filed Sep. 23, 1992 now abn., which was a continuation-in-part of application Ser. No. 07/873,416, filed Apr. 24, 1992, all now abandoned, and Ser. No. 07/781,063, filed Oct. 18, 1991, now U.S. Pat. No. 5,203,773.

BACKGROUND OF THE INVENTION

1. Field of the Invention

This invention relates to valve systems of the type adapted to allow the introduction of a surgical instrument into a patient's body. In particular, the invention is applicable to a cannula assembly wherein a cannula housing includes the valve assembly and the cannula is intended for insertion into a patient's body to sealingly accommodate an instrument inserted through the cannula and valve.

2. Background of the Prior Art

In laparoscopic procedures surgery is performed in the interior of the abdomen through a small incision; in endoscopic procedures surgery is performed in any hollow viscus of the body through narrow tubes or cannula inserted through a small entrance incision in the skin. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. Moreover, laparoscopic and endoscopic procedures often require the surgeon to act on organs, tissues, and vessels far removed from the incision, thereby requiring that any instruments used in such procedures be relatively long and narrow.

For such procedures, the introduction of a tube into certain anatomical cavities such as the abdominal cavity is usually accomplished by use of a trocar assembly comprised of a cannula assembly and an obturator. The cannula assembly includes a cannula tube attached to a valve assembly which is adapted to maintain a seal across the opening of the cannula assembly. Since the cannula tube is in direct communication with the internal portion of the valve assembly, insertion of the cannula tube into an opening in the patient's body so as to reach the inner abdominal cavity must maintain a relatively gas-tight interface between the abdominal cavity and the outside atmosphere.

Since surgical procedures in the abdominal cavity of the body require insufflating gases to raise the cavity wall away from vital organs, the procedure is usually initiated by use of a Verres needle through which a gas such as $CO_2$ is introduced into the body cavity. Thereafter, the pointed obturator of the trocar assembly is inserted into the cannula assembly and used to puncture the abdominal cavity wall. The gas provides a slight pressure which raises the inner wall surface away from the vital organs thereby avoiding unnecessary contact with the organs by the instruments inserted into the cannula. Following removal of the obturator, laparoscopic or endoscopic surgical instruments may then be inserted through the cannula assembly to perform surgery within the abdominal cavity.

In view of the need to prevent leakage of the insufflation gas from the cavity, the cannula is typically provided with a valve assembly which permits introduction of surgical instruments to provide selective communication between the inner atmosphere of the cavity with the outside atmosphere. In this regard, there have been a number of attempts in the prior art to provide such a seal as part of the cannula assembly.

One form of cannula valve assembly includes a flapper valve which is pivotally mounted within the cannula assembly and is automatically opened by the obturator or other object when it is inserted into the proximal end of the cannula. Conventional flapper valves may also be manually opened by pivoting a lever on the exterior of the housing. See, e.g., U.S. Pat. No. 4,943,280 to Lander. Trumpet valves are also known.

Other conventional cannula valve devices for accommodating surgical instruments include a single or plurality of flexible sealing members as shown, for example, in U.S. Pat. No. 4,655,752 to Honkanen et al., U.S. Pat. No. 4,909,798 to Fleischhacker, U.S. Pat. No. 4,673,393 to Suzuki et al., U.S. Pat. No. 4,610,665 to Matsumoto et al., and U.S. Pat. No. 4,869,717 to Adair.

Further, typical hemostasis valve devices are shown, for example, in U.S. Pat. No. 5,041,095 to Littrell, and U.S. Pat. No. 5,000,745 to Guest et al., While attempts have been made to provide a valve assembly which maintains the integrity of the seal between the body cavity and the atmosphere outside the patient's body. Seal systems provided to date have failed to address the full range of surgeons' needs, especially when instruments varying in diameter are used. Specifically, sealing elements currently used may be damaged when an instrument, such as a pointed obturator is passed therethrough. Moreover, present seal systems have not provided adequate sealing about an instrument before and after an instrument is passed therethrough. Also, existing seal systems have failed to provide adequate sealing of a cannula, or a trocar assembly having a cannula which accommodates instruments of varying diameters. It is a further disadvantage of existing seal systems that adequate sealing is not provided in conjunction with a structure for holding a cannula in a desirable position in an incision with respect to a patient's body.

It would therefore be desirable to provide a valve assembly which addresses these shortcomings in the art by maintaining a substantially fluid tight seal between an internal portion of a patient's body and the outside atmosphere during insertion and manipulation of a surgical instrument into the patient's body. Such an assembly may further provide stabilization or lateral limitation of motion of an instrument passed therethrough. Also, the valve assembly may inhibit fluids from exiting with the instrument while being withdrawn, and the valve assembly may inhibit contact with sealing structure. It is further desirable to provide a valve assembly for use with a cannula or trocar assembly which provides substantial fluid and gas tight sealing before and after an instrument is passed therethrough. It would also be desirable to provide a cannula which maintains a predetermined position of a cannula or trocar assembly in an incision.

The present invention provides a valve assembly which may be incorporated into a cannula assembly or utilized in combination with any type of tubular member for providing access into the body of a patient while permitting introduction of instruments through the valve assembly into the body. The valve assembly includes a sealing gasket which provides a desirable seal about an instrument inserted through the valve assembly. The valve assembly may further provide stabilization of the cannula or limit lateral motion of the cannula when an instrument is passed therethrough.

Also, the valve assembly may include more than one sealing element providing improved sealing qualities under varied conditions. At all times, the surgeon maintains control over the interface between the atmospheres within and without the patient's body. Moreover, the present invention makes it possible to introduce instruments of varying sizes into the body and insures the maintenance of a gas seal despite instrument manipulation therethrough.

SUMMARY OF THE INVENTION

A valve assembly is provided for permitting the introduction of a surgical instrument into a patient's body through a tube such as a cannula. The valve assembly includes at least one sealing gasket constructed of a flexible material and having a passageway. The passageway is substantially closed prior to insertion of an instrument through the valve assembly forming a substantial gas tight seal. When an instrument is inserted through the passageway of the valve assembly the flexible material defining the passageway resiliently engages an outer surface of the instrument in a substantially gas tight manner.

The sealing gasket may include sealing structure having first and second overlapping elements. The sealing gasket can be removably positioned on a frame or in a housing assembly such that the first and second overlapping elements are tensioned.

The valve assembly may further include sealing structure comprising a third element having a substantially central aperture. The third element may have a tapered portion and be constructed at least partially of a flexible material. The third element accommodates an instrument passed through its central aperture providing substantial sealing about the instrument passed therethrough. A retainer structure inhibits contact by the instrument with adjacent sealing structure such as, the first and second elements of the gasket assembly or the third element. The retainer structure includes at least one movable portion and a substantially central aperture for accommodating the instrument.

The valve assembly may further provide a sealing structure comprising a fourth element for substantially removing fluids from the surface of an instrument passed therethrough. The fourth element may include a substantially central aperture defined by a deformable material such that the central aperture is capable of accommodating the instrument.

BRIEF DESCRIPTION OF THE DRAWINGS

The foregoing features of the present invention will become more readily apparent and will be understood by referring to the following detailed description of preferred embodiments of the invention, which are described hereinbelow with reference to the drawings wherein.

DETAILED DESCRIPTION OF THE PREFERRED EMBODIMENTS

The present invention contemplates introduction into a patient's body of all types of surgical instruments including, but not limited to clip appliers, lasers, photographic devices, graspers, scissors, tubes, and the like. All of such objects are referred to herein as "instruments".

Figure 1:
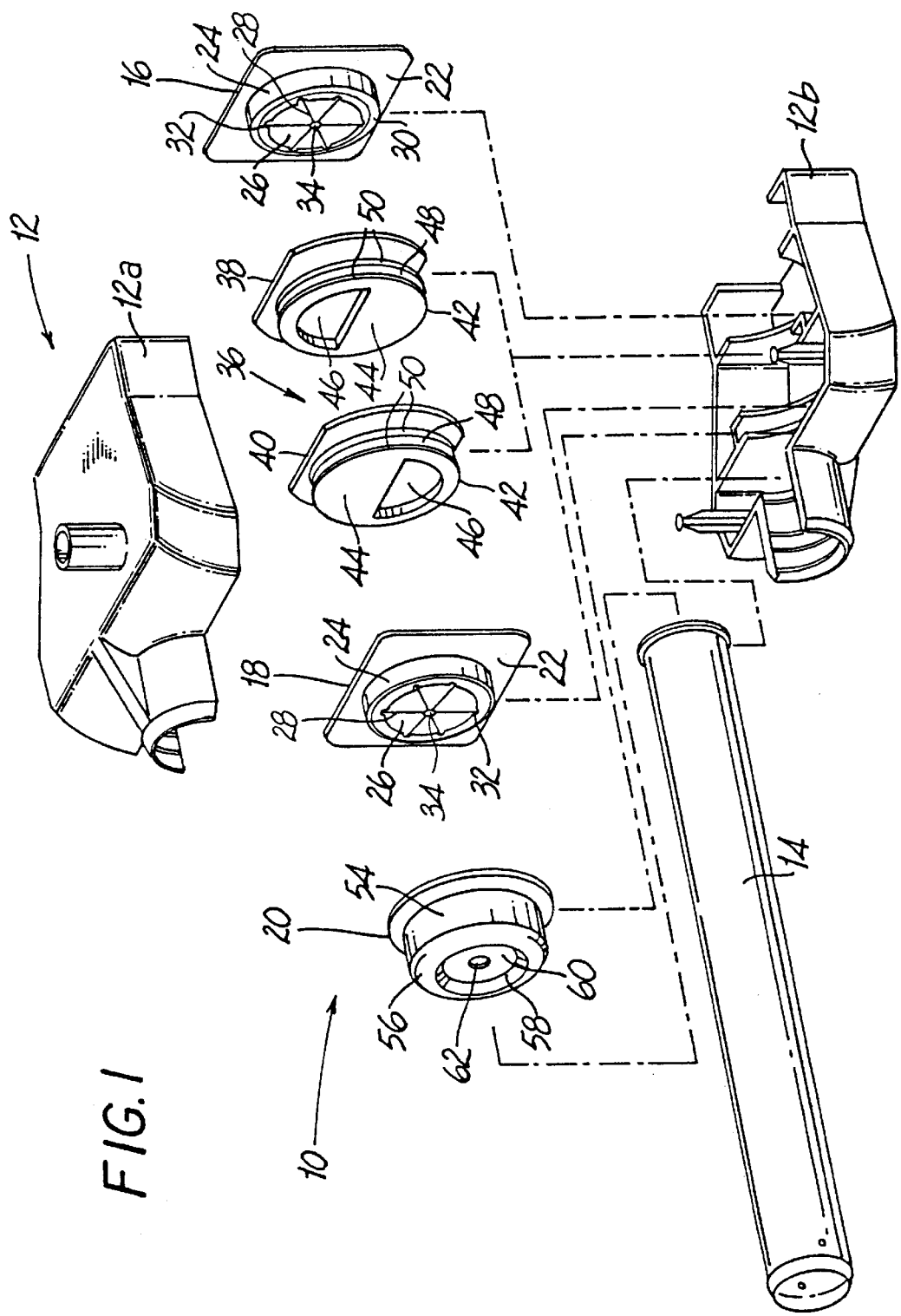
FIG. 1 is an exploded perspective view of a cannula assembly illustrating a valve assembly according to the present invention.
Figure 2:
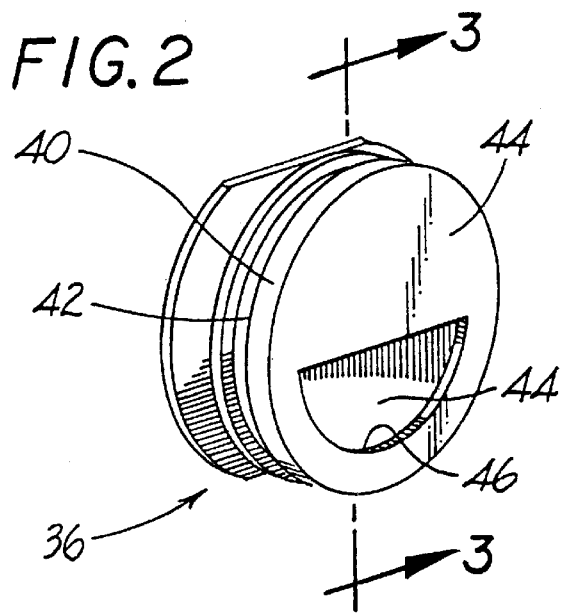
FIG. 2 is a perspective view illustrating a sealing gasket assembly shown as part of the valve assembly illustrated in FIG. 1.
Figure 3:
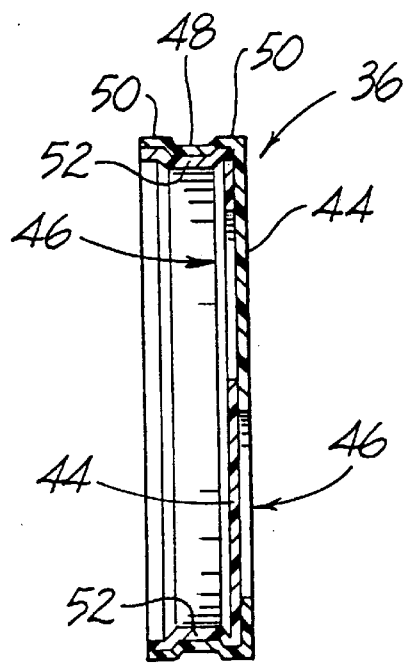
FIG. 3 is a cross-sectional view of the sealing gasket assembly taken along line 3—3 in FIG. 2.

Referring to the drawings, in which like reference numerals identify identical or similar elements, FIGS. 1–3 illustrate a preferred embodiment of a valve assembly 10. The valve assembly 10 is incorporated into a cannula valve housing 12 having an upper half 12a and a lower half 12b attached at the proximal end of the cannula 14. The valve assembly 10 provides a substantial seal between a body cavity of a patient and the outside atmosphere before and after an instrument is inserted through the cannula valve housing 12. Moreover, each of the valve assemblies of the present invention is capable of accommodating instruments of varying diameters, e.g., from 3 mm to 15 mm, by providing a gas tight seal with each instrument when inserted, and returning to a fully sealed configuration upon removal of the instrument in the valve assembly. This flexibility of the present valve assembly greatly facilitates endoscopic surgery where a variety of instruments having differing diameters are often needed during a single surgical procedure.

Referring to FIG. 1, the valve assembly 10 includes a first retainer 16 at its proximal end and a second retainer 18 distal to the first retainer 16 and proximal a bellows seal 20. The retainers 16, 18 are preferably formed of a suitable synthetic resin or plastic, such as polypropylene. The first and second retainers 16, 18 are essentially identical and both preferably include generally rectangular plates 22 having integrally molded circular body portions 24 extending orthogonally from the rectangular plates 22. The body portion 16 mates with the proximal side of the sealing gasket assembly 36.

Although the plates 22 are generally rectangular shaped in the preferred embodiments described herein and shown in the accompanying drawings, any plate shape may be desirable, such as, for example circular shaped. Further, other geometric configurations of the body portion 24 may be contemplated or, for example, the body portion 24 itself may be eliminated by attaching the movable portions 26 (described below) to the plate 22.

Figure 6:
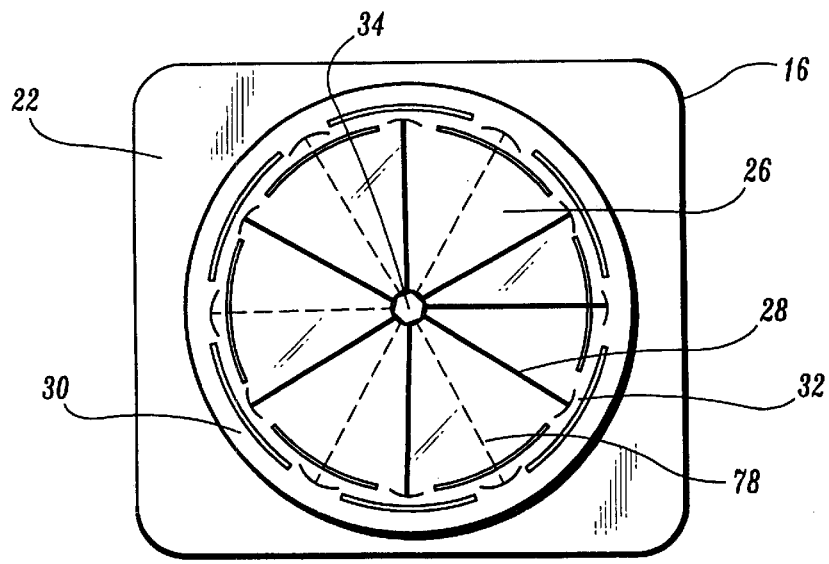
FIG. 6 is a front elevational view illustrating a rectangular retainer and a circular retainer in a coupled configuration.

As best seen in FIG. 6, preferably a plurality of triangularly shaped movable portions 26 are divided by a series of slits 28 and are attached to the perimeter 30 of the body portions 24 of the retainers 16, 18 by hinge regions (FIG. 1) 32. The slits 28 extend radially outward from central aperture 34 of the retainers 16, 18.

A sealing gasket assembly 36, FIGS. 1–4 distal to the first retainer 16 and preferably includes identical first and second elements 38, 40 made of a flexible resilient material. Preferably, both the first and second elements 38, 40 include a substantially circular body 42 having a wall 44 defining a semi-circular opening 46. As shown in FIG. 3, the outer perimeter of the body includes a groove 48 defined by two ridges 50. The groove on the outer perimeter defines a ridge 52 on the inner circumference of the body 42 (FIG. 3).

Although the sealing gasket assembly includes a substantially circular body as described in the preferred embodiments herein and illustrated in the accompanying drawings, the sealing gasket assembly may include a body having a different geometric configuration, such as, for example, a rectangular shape. Additionally, although sealing gasket assembly 36 is described in the preferred embodiments herein as consisting of first and second elements 38, 40, it is also contemplated that first element 38 may have a semi-circular wall of similar configuration to wall 40 bonded to the circumference of first element 38 to create two overlapping members. This approach eliminates one structure from the overall valve assembly.

As shown in FIGS. 1 and 3, the first and second elements 38, 40 cooperate by positioning the semi-circular opening 46 in each element radially opposite each other. Thus, the second element 40 fits over the first element 38 in overlapping relation such that the wall 44 of the first element 38 covers the opening 46 in the second element 40, 10 and the wall 44 of the second element 40 covers the opening 46 of the first element 38. Further, the ridge 52 on the inner circumference of the second element 40 mates with the groove 48 in the first element 38. The sealing gasket assembly 36 provides a substantially fluid tight seal before instrument insertion.

Figure 4:
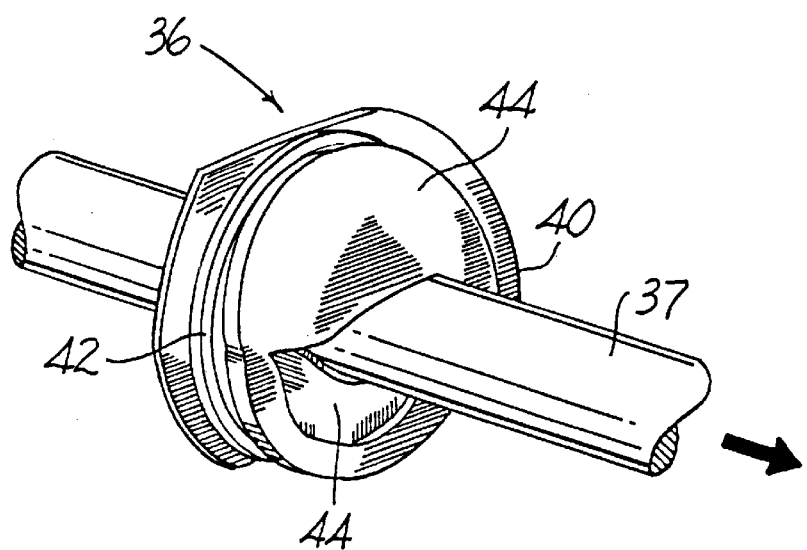
FIG. 4 is a perspective view of the sealing gasket assembly during the insertion of an instrument.

The flexible material allows the sealing gasket assembly 36 to accommodate instruments of varying sizes, e.g., diameters of from 3 mm to 15 mm. The sealing gasket assembly is preferably made of a flexible material having a durometer in the range of 25–35, and most preferably a durometer of 30. As shown in FIG. 4, flexible resilient walls accommodate an instrument 37 by resiliently deforming to enable the instrument 37 to pass therethrough. Upon removal of instrument 37, sealing gasket assembly 36 returns to its initial position, thereby reestablishing a substantially fluid tight seal. To facilitate and ensure that the fluid tight seal is reestablished upon instrument removal, it is preferred that walls 44 be placed under tension, thereby creating a tautness which further biases walls 44 toward their initial overlapping, abutting relation. This tension may be created by molding elements 38 and 40 of a slightly smaller diameter than the matable portion of retainer 16, and then stretching elements 38 and 40 to mate therewith.

The bellows seal 20 (FIG. 1) is positioned distally adjacent the second retainer 18 and is made of a suitable flexible resilient material. The bellows seal 20 is preferably formed of an elastomeric material such as, preferably, natural rubber. The bellows seal 20 has a generally circular body 54 and includes a circumferential ridge 56 positioned at its distal end. The ridge 56 defines the perimeter 58 of a recessed portion 60 having a substantially central aperture 62.

The bellows seal 20 is adapted to accommodate an instrument through its central aperture 62. The flexible material enables the aperture 62 to accommodate instruments of varying sizes while providing a substantially fluid and gas tight seal about the instrument, e.g., instruments having diameters of from 3 to 15 mm. The size of the aperture in the bellow seal is preferably from 2.5 mm to 3.0 mm (0.10 inches to 0.12 inches). The material of the bellows seal preferably has a durometer value in the range of 35 to 45, and most preferably a durometer value of 40.

When accommodating an instrument through the aperture 62 of the bellows seal 20, the ridge 56 allows the recessed portion 60 surrounding the aperture 62 to accommodate the instrument while substantially encouraging the retention of the circular shape of the aperture. Further, the ridge 56 substantially reduces the chances, for example, of sealing integrity being compromised by instrument manipulation, or of the bellows seal material tearing. The bellows seal 20 as described in the preferred embodiments herein and illustrated in the accompanying drawings, could be any deformable sealing element which includes, for example, a different geometric aperture configuration.

In operation, referring to FIGS. 1 and 4, the first retainer 16 guides the instrument as it is being inserted through the valve assembly 10. The first and second retainers 16, 18 encourage the instrument through the valve assembly by assisting the adjacent sealing gasket assembly 36 and the bellows seal 20 to accommodate the instrument. The triangular portions 26 of the retainers 16, 18 displace the flexible resilient material of the adjacent sealing gasket assembly 36 and bellows seal 20 encouraging easier access for the instrument.

Further, the triangular movable portions 26 of the retainers 16, 18 discourage unwanted contact between the instrument, such as a trocar obturator having a sharp tip, and the sealing gasket assembly 36 and the bellows seal 20 by, for example, providing an intermediate surface between the sharp instrument being inserted into the valve assembly 10 and the adjacent sealing gasket assembly 36 and bellows seal 20. Both retainers provide support to the valve assembly such that manipulation of the instrument will not deter the instrument from the desired passageway, or compromise the valve assembly's sealing effect.

Although the gasket seal assembly is proximal the bellows seal as described herein and shown in the accompanying drawing of the preferred embodiments, the order may be reversed as desired.

Figure 5:
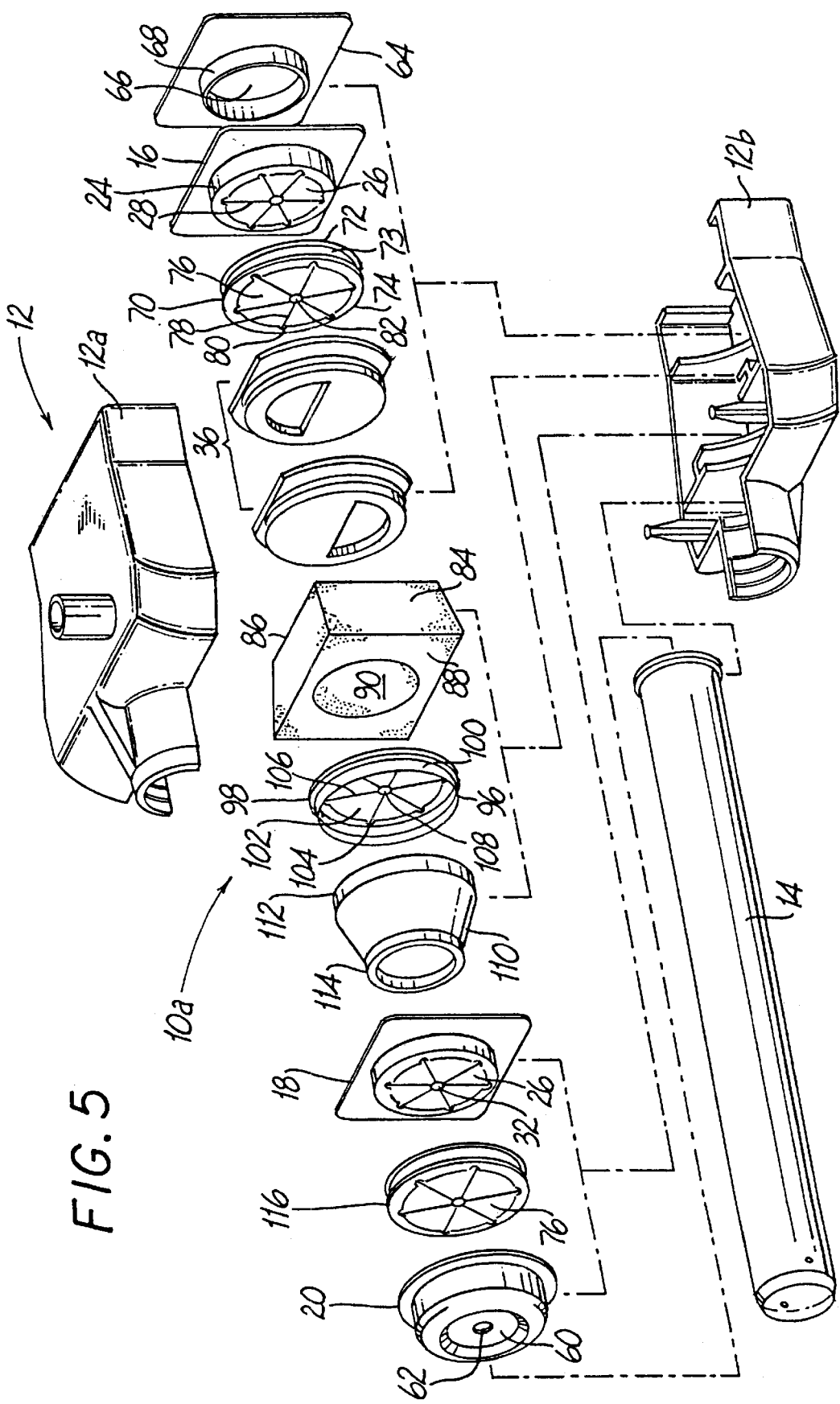
FIG. 5 is an exploded perspective view of a cannula assembly illustrating the valve assembly according to another embodiment of the present invention.

Another embodiment of the valve assembly is shown in FIG. 5. The valve assembly 10a is similar to the previous embodiment shown in FIG. 1, however, the embodiment shown in FIG. 5 includes, in addition to other elements contributing to the sealing function of the valve assembly, a stabilizer plate 64 at its proximal end. The stabilizer plate 64 has a substantially central circular aperture 66 therethrough to accommodate a surgical instrument. An integrally molded lip portion 68 extends outwardly from the plane of the stabilizer plate further defining the aperture. The stabilizer plate 64 provides rigidity to the overall valve assembly 10*a*, and further guides the instrument through a desired passageway in the valve assembly 10*a*.

A first rectangular retainer 16 is distally adjacent to the stabilizer plate 64. The first rectangular retainer 16 includes a circular body portion 24 which fits over the lip portion 68 of the stabilizer plate 64 and preferably frictionally engages lip portion 68. The first rectangular retainer 16 is essentially identical to, and functions as described in the previous embodiment shown in FIG. 1; however, in the present embodiment the first rectangular retainer 16 communicates with a first circular retainer 70.

Figure 7:
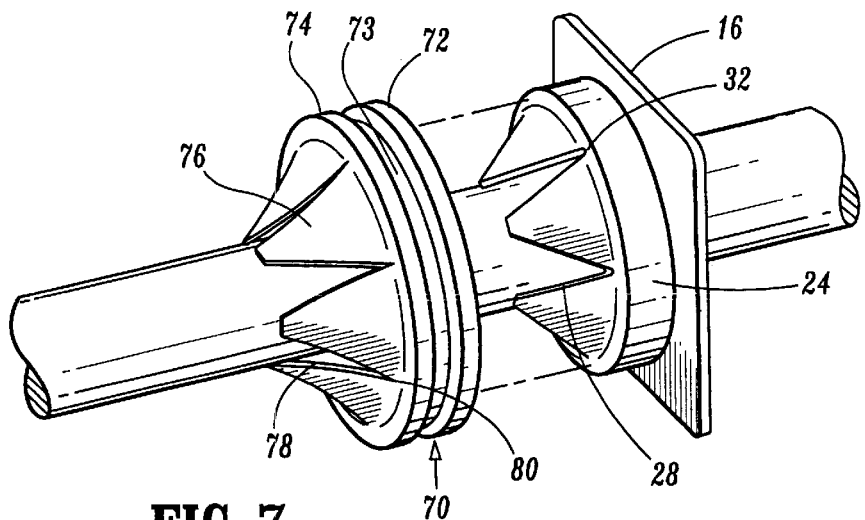
FIG. 7 is an exploded perspective view illustrating the rectangular retainer and the circular retainer during the insertion of an instrument.

Referring to FIG. 7, the first circular retainer 70 includes a proximal and a distal ridge 72, 74 positioned about the perimeter and defining a groove 73 therebetween. Similar to the first rectangular retainer 16, the first circular retainer 70 includes a plurality of triangular portions 76 divided by a series of slits 78 which are connected to the distal ridge 74 by hinge regions 80. The slits 78 extend radially from a substantially central aperture 82 (FIG. 5), and the first circular retainer 70 is dimensioned to fit over and preferably frictionally engage the body portion 24 of the first rectangular retainer 16. The first rectangular retainer 16 and the first circular retainer 70 are juxtapositioned such that the slits 78, 28 of one of the retainers transect the triangular portions 26, 76 of the other retainer. For example, the retainers may be juxtapositioned such that the slits 78 of the first circular retainer 70 overlappingly transect the triangular portions 26 of the first rectangular retainer 16.

The sealing gasket assembly 36 (FIG. 5) is positioned distal to the retainers 16, 70 and is identical to the sealing gasket assembly 36 described in the previous embodiment illustrated in FIGS. 1–4 and associates similarly with the retainer members. In the present embodiment, however, the sealing gasket assembly 36 is positioned proximal to a foam block 84.

Figure 8:
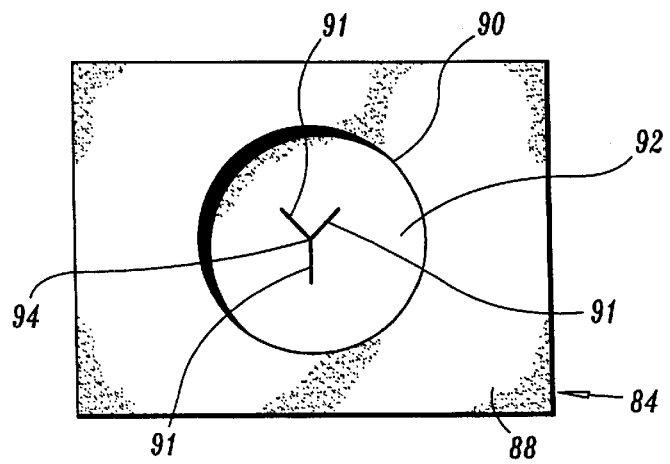
FIG. 8 is a front elevational view of a foam block shown as part of the valve assembly illustrated in FIG. 5.

The foam block 84 (FIGS. 5 and 8) includes a generally rectangular proximal face 86 and tapers generally outwardly from a longitudinal center line to a rectangular distal face 88. The foam block 84 includes a circular region 90 in its distal end partially extending therethrough to an end wall 92. The end wall 92 includes an aperture extending through the proximal face which is defined by three slits 91 converging at a center point 94, and biased closed by the foam, as shown in FIG. 8. When an instrument is passed through the aperture the foam accommodates the instrument. Further, the foam block 84 biases the sealing gasket assembly 36 in the closed position and encourages the sealing gasket assembly 36 to resiliently assume the closed position after an instrument has been removed.

A distal retainer 96 (FIG. 5) is generally circular and is positionable inside the aperture in the foam block 84. The distal retainer 96 includes a circumferential ridge 98 and a flange 100 extending orthogonally to the plane of the distal retainer 96. Similar to the first circular retainer 70, the distal retainer 96 includes a plurality of triangular portions 102 attached about the perimeter of the retainer by hinge regions 104. A plurality of slits 106 define the triangular portions 102 and the slits extend radially from a central aperture 108.

A second stabilizer 110 is adjacent to the distal retainer 96 and tapers generally inwardly towards a longitudinal center line from its proximal end. The proximal end 112 of the second stabilizer mates with the distal retainer 96 and the distal end 114 of the second stabilizer mates with the second rectangular retainer 18 (described below). The second stabilizer 110 provides guidance to the instrument as it passes through the valve assembly. The first stabilizer plate 64 and the second stabilizer 110 align the instrument and generally provide support for the entire valve assembly 10*a*.

A second rectangular retainer 18 and a second circular retainer 116 are positioned distal to the second stabilizer 110. The second retainers 18, 116 are essentially identical to the first rectangular and circular retainers 16, 70, are combined in an identical manner, and function similarly.

A bellows seal 20 is positioned distal to the second retainers 18, 116 and mates with the second circular retainer 116. The bellows seal 20 is identical to the bellows seal described in the previous embodiment illustrated in FIG. 1, and functions similarly.

In operation, referring to FIG. 5, a surgical instrument (not shown) may be inserted at the proximal end of the cannula housing 12. The first and second rectangular retainers 16, 18, the sealing gasket assembly 36, and the bellows seal 20, operate essentially the same as described in the previous embodiment illustrated in FIG. 1. In the present embodiment, however, the stabilizer plate 64 receives the instrument and guides the instrument into the valve assembly 10*a*. As shown in FIG. 7, as an instrument passes through the first and second rectangular and circular retainers 16, 70, 18, 116 the triangular plates 26, 76 pivot distally from a longitudinal center line of the retainers. As in the previous embodiment illustrated in FIG. 1, the retainers encourage the instrument through the sealing gasket assembly 36 and the bellows seal 20 by urging the flexible materials of the sealing gasket assembly and the bellows seal to accept the instrument.

Further, the rectangular and circular retainer combination 16, 70, 18, 116, are juxtapositioned such that the slits of one retainer transect the triangular portions of the other, as shown in FIGS. 6 and 7. This overlapping arrangement more effectively discourages unwanted contact between the instrument and the other members of the valve assembly. For example, the retainers 16, 70, 18, 116 provide an interface between a pointed instrument being inserted into the valve assembly and the adjacent sealing gasket assembly or bellow seal, i.e., as the instrument projects into the slit 28 of the rectangular retainer 16, 18, the circular retainer's triangular portions 76 extend between the instrument and the seal 36, 20.

The instrument passes through the aperture of the foam block 84, which is biased closed, through deformation and compression of the flexible resilient foam so as to accommodate the instrument. After the instrument is removed, the foam block 84 encourages the sealing gasket assembly 36 to return to its original position.

The distal retainer 96 is essentially identical to the first circular 70 and second circular retainers 116. The distal retainer is designed to fit into the circular region 90 in the foam block. The distal retainer 96 operates as the retainers 16, 70 discussed above for discouraging unwanted contact between the instrument and the foam block 84.

Figure 9:
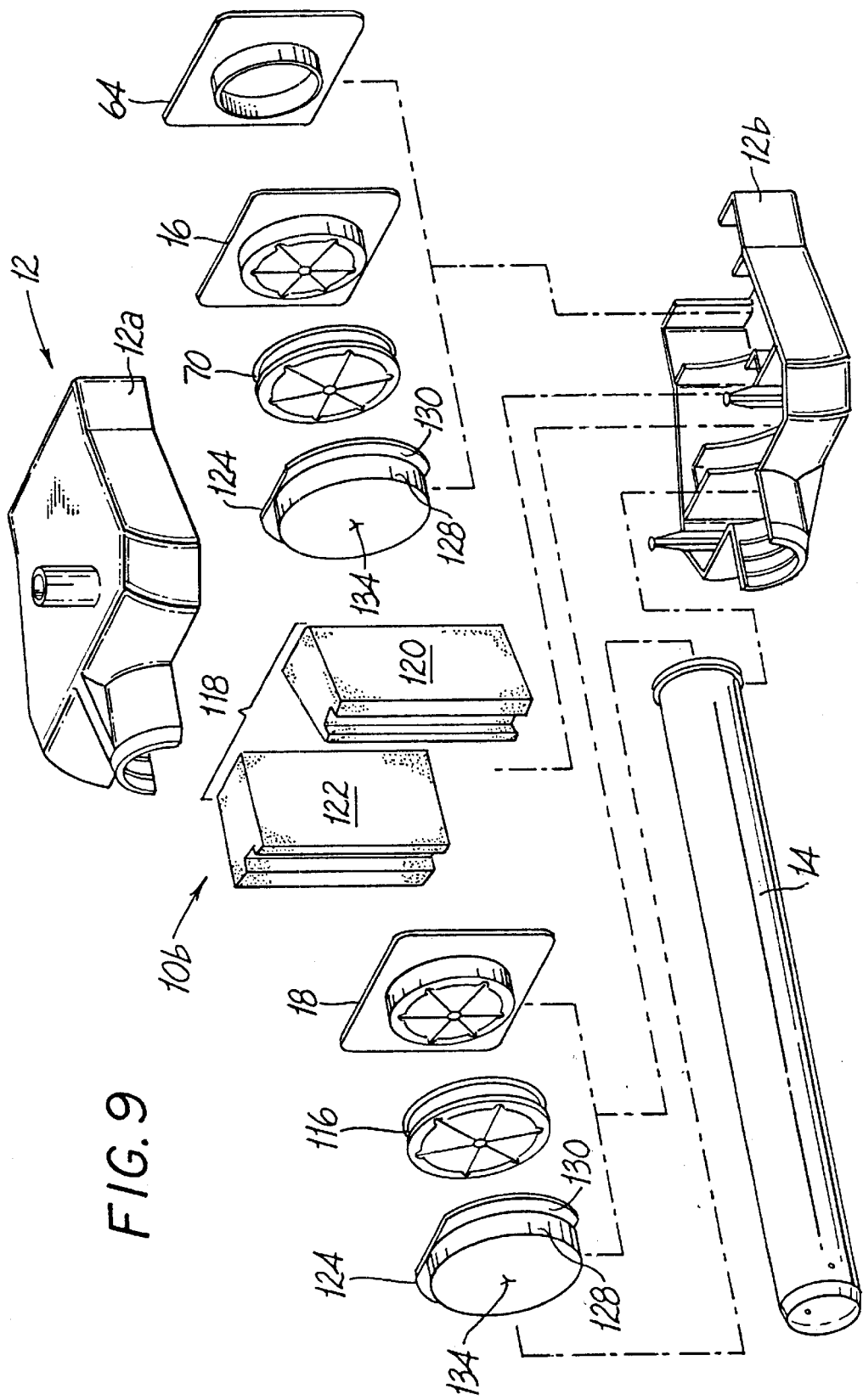
FIG. 9 is an exploded perspective view of a cannula assembly illustrating the valve assembly according to another embodiment of the present invention.

Another embodiment of the valve assembly positioned in a cannula housing 12 is shown in FIG. 9. The valve assembly 10*b* is essentially the same as the previous valve assembly 10*a* shown in FIG. 5; however, the embodiment illustrated in FIG. 9 includes a foam member 118 having two portions 120, 122, and two single element gasket seals 124 positioned distal to first retainers 16, 70 and distal to second retainers 18, 116, respectively.

The two portions 120, 122 of the foam member 118 are in side-by-side abutting relation inside the cannula valve housing 12. The two portions 120, 122 are biased towards each other by communicating with the walls of the cannula valve housing 12. An instrument, however, may pass between the two portions 120, 122 of the foam member 118 by displacing the flexible resilient foam.

The two piece resilient foam member 118 biases the adjacent single element gasket seal 124 in a closed or rest position. After the withdrawal of an instrument, the foam member 118 urges the single element gasket seal 124 to return to its rest position.

Preferably, both the single element gasket seals 124 include a generally circular body 128 having a flange 130 at its proximal end extending radially outwardly. A central passageway 134 is biased closed by the resiliency of the material and is defined by three slits converging at a center point. As an instrument is passed through the aperture 134 defined by the three slits the resilient material accommodates the instrument. After the instrument has been removed the resilient material of the single element gasket seals 124 return to its original configuration. The single element gasket seal 124 proximal the foam member 118, for example, may accommodate a partially inserted instrument while the distal single element gasket seal 124 remains in a closed or at rest position.

The first stabilizer plate 64, the first and second rectangular retainers, 16, 18 and the circular retainers, 70, 116 are essentially the same as described in the previous embodiment illustrated in FIG. 5 and operates similarly.

The valve assembly described in the preferred embodiments and illustrated in the accompanying drawings is preferably capable of accommodating instruments varying in diameter from 3 mm to 15 mm, and most preferably diameters from 5 mm to 12 mm. When inserting the instrument into the valve assembly as described herein the insertion force, i.e., the axial force asserted against the instrument to pass the instrument into and through the valve assembly is preferably kept to a minimum.

For example, preferable insertion forces of approximately no more than 5 pounds are desirable for instruments having approximate diameters of more than 9 mm. Most preferably, insertion forces of approximately no more than 4 pounds are desirable for instruments having approximate diameters of between 5 mm and 8 mm.

Moreover, preferable insertion forces of approximately 7 pounds are desirable for instruments having approximate diameters of no more than about 15 MM e.g., diameters of 9 mm to 15 mm. Most preferably, insertion forces of approximately no more than 6 pounds are desirable for instruments having approximate diameters of between 10 mm and 12 mm.

Figure 10:
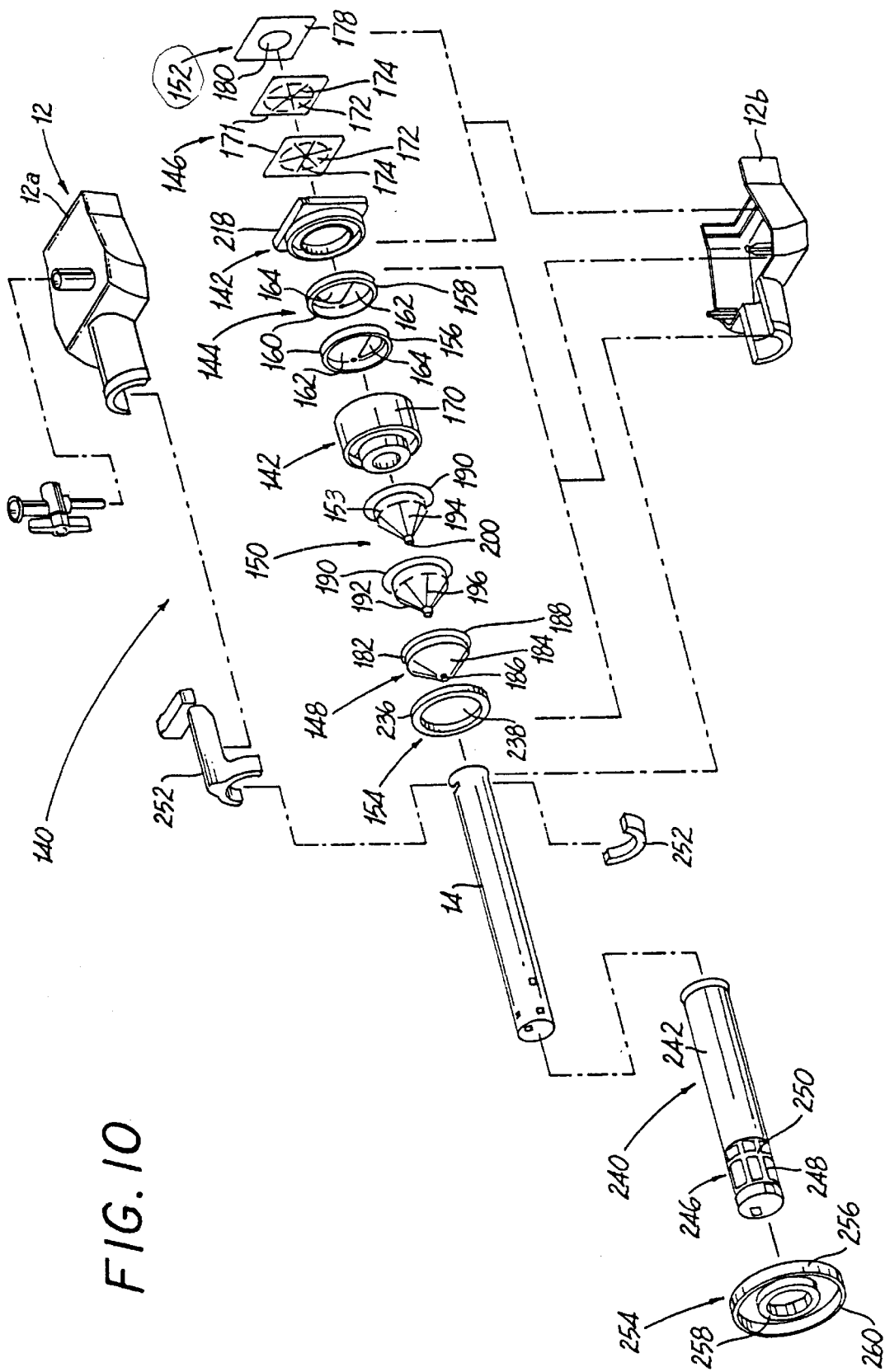
FIG. 10 is an exploded perspective view illustrating a cannula and valve assembly according to the present invention.
Figure 15:
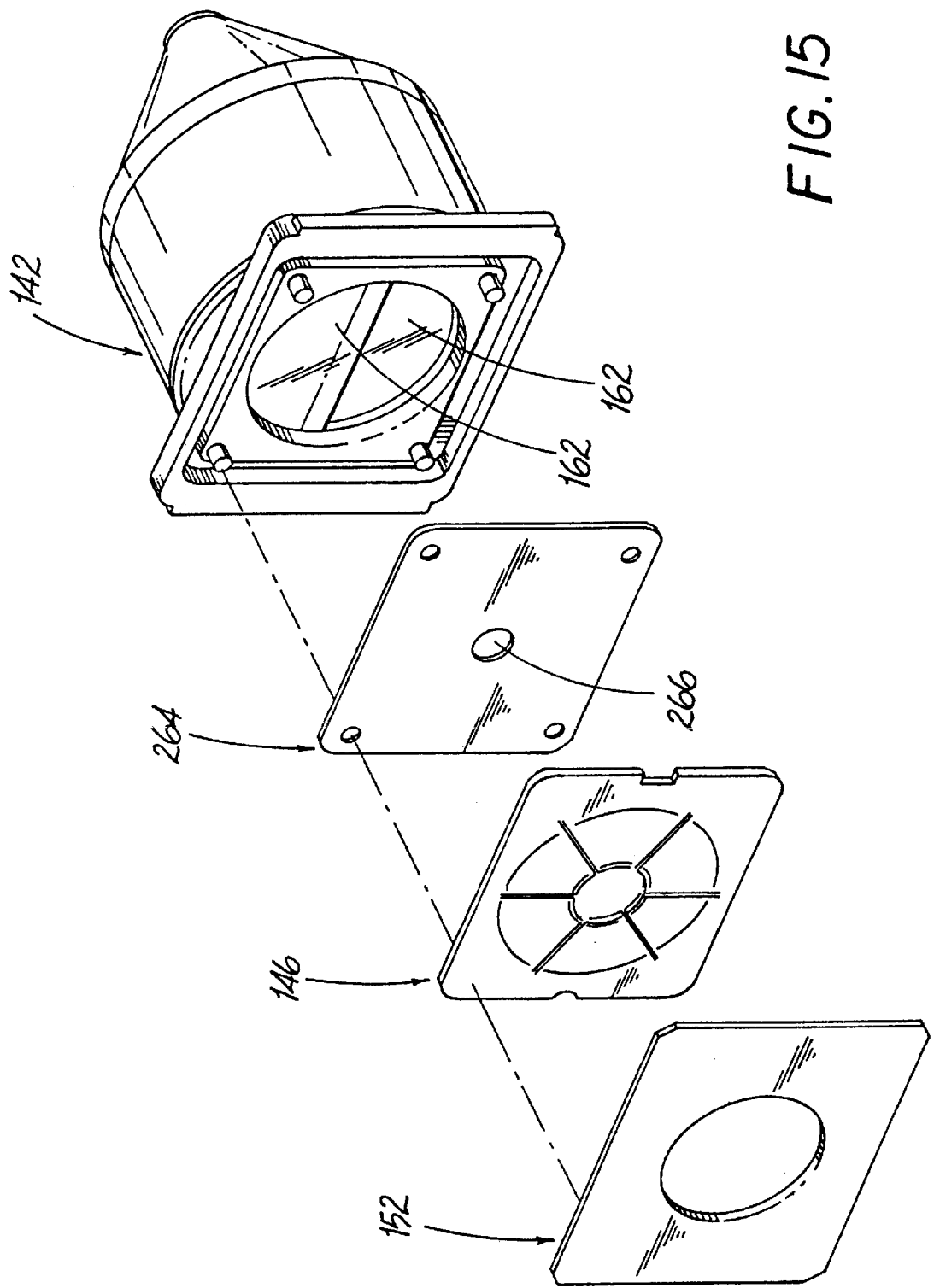
FIG. 15 is an exploded perspective view illustrating a valve assembly according to another embodiment of the present invention.
Figure 16:
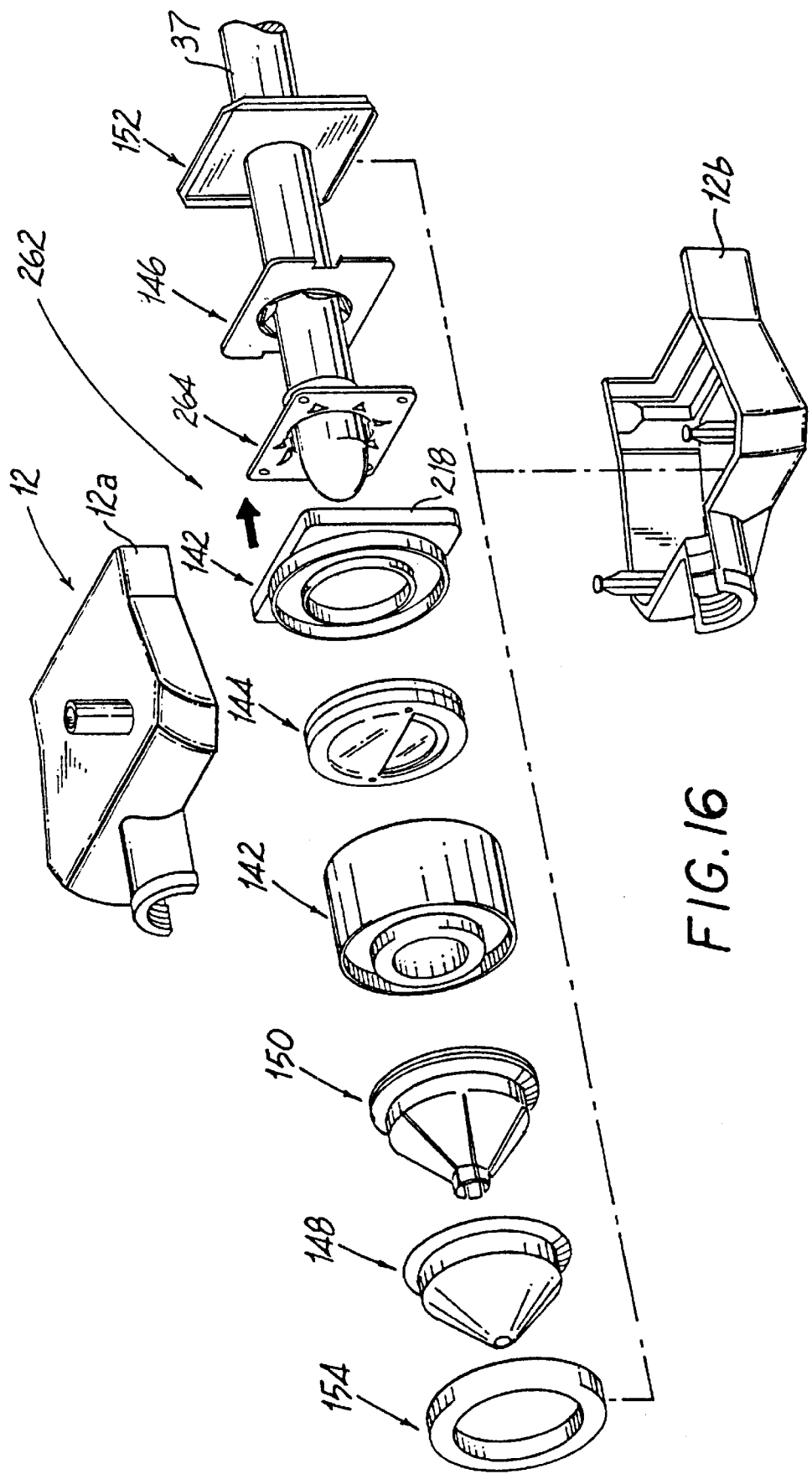
FIG. 16 is an exploded perspective view of a cannula assembly illustrating the valve assembly of FIG. 15 during the withdrawal of an instrument.
Figure 17:
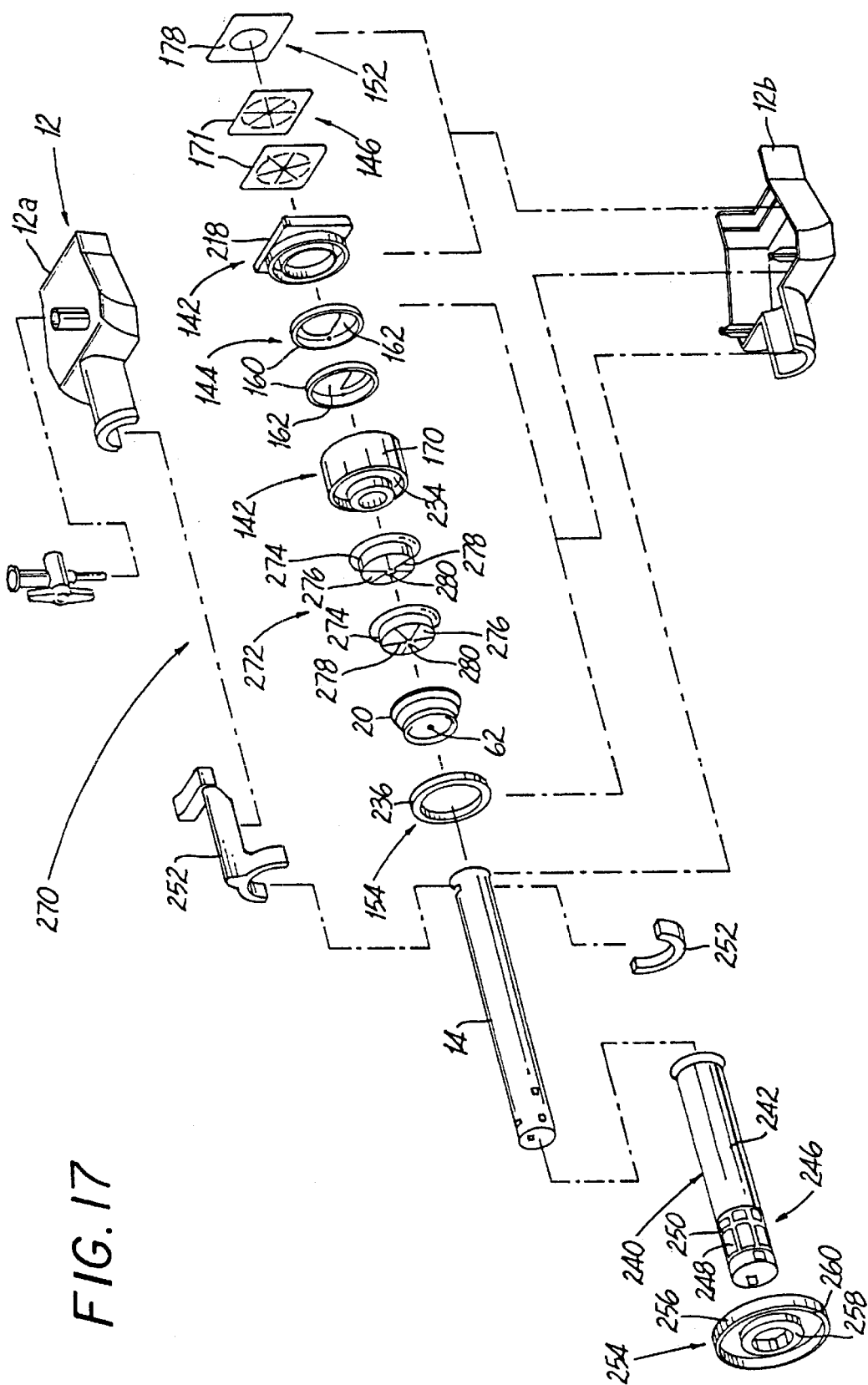
FIG. 17 is an exploded perspective view illustrating a cannula and valve assembly according to another embodiment of the present invention.

Referring to FIGS. 10–20, several embodiments of a valve assembly according to the present invention are illustrated. In each embodiment the valve assembly includes sealing structure having at least three elements which contribute to the sealing function of the assembly. The valve assembly is incorporated into a cannula valve housing 12 having an upper half 12a and a lower half 12b attached at the proximal end of the cannula 14 which is configured as an elongated tubular member, and also shown in FIGS. 1, 5 and 9. A tissue gripping apparatus 240 and a cannula member 254, as shown in FIGS. 10 and 17, may be attached to the cannula 14. The cannulas proximal end is closest to the surgeon and its distal end is opposite the proximal end. Both the distal and proximal ends of the cannula are referred to herein for reference.

The valve assemblies shown in FIGS. 10–20 provide a substantial seal between a body cavity of a patient and the outside atmosphere before and after an instrument is inserted through the cannula valve housing 12. Moreover, each of the embodiments of the valve assemblies are capable of accommodating instruments of varying diameters, e.g., from 3 mm to 15 mm, by providing a substantial gas and fluid tight seal before and after instrument insertion. This instrument accommodating flexibility of the present valve assemblies greatly facilitates endoscopic surgery where a variety of instruments having differing diameters are often needed during a single surgical procedure.

Referring to FIGS. 10–14, a preferred embodiment of a valve assembly 140 includes a two piece housing assembly 142, sealing structure comprising a sealing gasket assembly 144 having first and second elements, and sealing structure further comprising a third sealing element embodied as a conical seal 148, conical retainers 150, square retainers 146, a stabilizer plate 152, and a fastening ring 154.

The sealing gasket assembly 144 of the valve assembly 140 is positioned in the housing assembly 142. The sealing gasket assembly 144 may include characteristics similar to sealing gasket assembly 36 described above and shown in FIGS. 1–5.

Specifically, the sealing gasket assembly 144 preferably includes identical first and second overlapping sealing elements 156, 158 made of a flexible resilient material. Preferably, both the first and second sealing elements 156, 158 include a circumferential ridge 160 and a wall 162 enclosed by the ridge 160. Each wall 162 includes a semi-circular opening 164.

Figure 11:
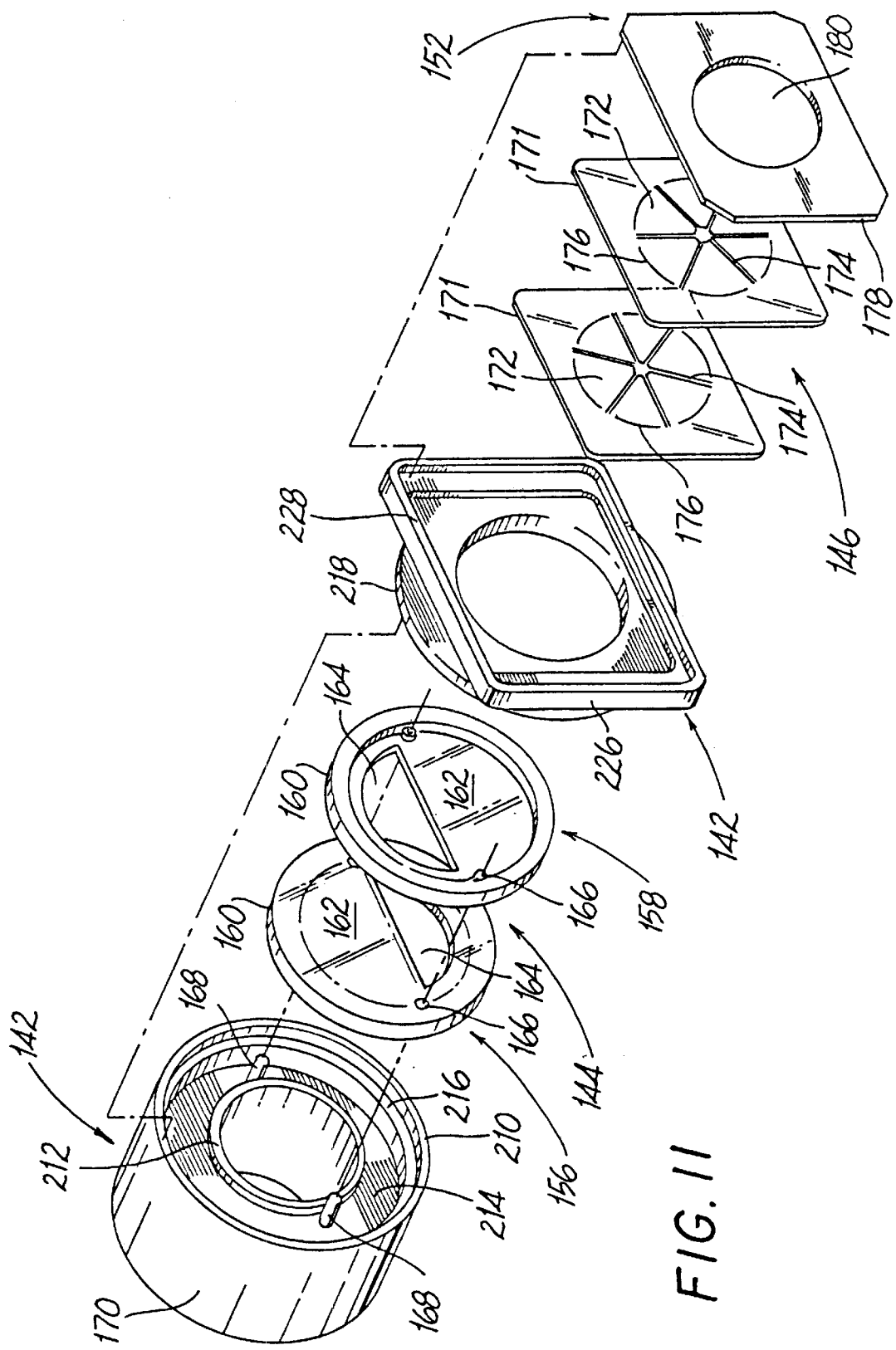
FIG. 11 is an exploded perspective view illustrating a housing assembly of the valve assembly shown in FIG. 10.

Each of sealing elements 156, 158 includes a pair of radially opposed holes 166, as best seen in FIG. 11. The holes 166 mate with the pins 168 of the cylindrical body portion 170 of the two piece housing assembly 142. Although the sealing gasket assembly 144 is shown being attached to the housing assembly 142 by pins 168, other methods may be used, such as, for example, adhesives.

The flexible nature of the elements 156, 158 of the sealing gasket assembly 144 enable the elements 156, 158 to mate with one another by stretching one element over the other. The elements 156, 158 cooperate by positioning the semi-circular opening 164 in each element 146, 158 radially opposite each other. Thus, the first and second sealing elements 156, 158 mate in overlapping relation such that the wall 162 of one element overlaps the semi-circular opening 164 of the other element.

The overlapping sealing elements 156, 158 define a sealable passageway therethrough. The flexible nature of the walls 162 allow the sealing gasket assembly 144 to deformably accommodate an instrument passed therethrough. Moreover, the walls 162 resiliently return to their original position after removal of an instrument. Thus, the overlapping relation of the elements of the sealing gasket assembly 144 provides a substantially fluid tight seal before instrument insertion and helps to discourage fluid passage around an instrument passed through the sealing gasket assembly 144.

The sealing gasket shown FIGS. 10–14, as with the previous sealing gasket shown in FIGS. 1–5, includes flexibly resilient material allowing the sealing gasket assembly 36 to accommodate instruments of varying sizes, e.g., diameters of from 3 mm to 15 mm. The sealing gasket assembly 144 is preferably made of a flexible material having a durometer valve in the range of 25–35, and most preferably a durometer valve of 30.

To facilitate and ensure that the fluid tight seal is reestablished upon instrument removal, it is preferred that walls 162 of the elements 156, 158 be placed under tension, thereby creating a tautness which further biases walls 162 toward their initial overlapping, abutting relation.

The tensioning of the overlapping sealing elements 156, 158 further encourages the overlapping elements 156, 158 to surround an instrument passed therethrough. The overlapping elements 156, 158 are biased in an overlapping abutting relation to substantially discourage gas and fluid leakage through the valve assembly. When an instrument is inserted through the passageway, the flexible overlapping elements 156, 158 accommodate and substantially surround the outer surface of the instrument. The flexible nature of the overlapping elements surround the instrument providing substantial gas and fluid sealing.

Figure 12:
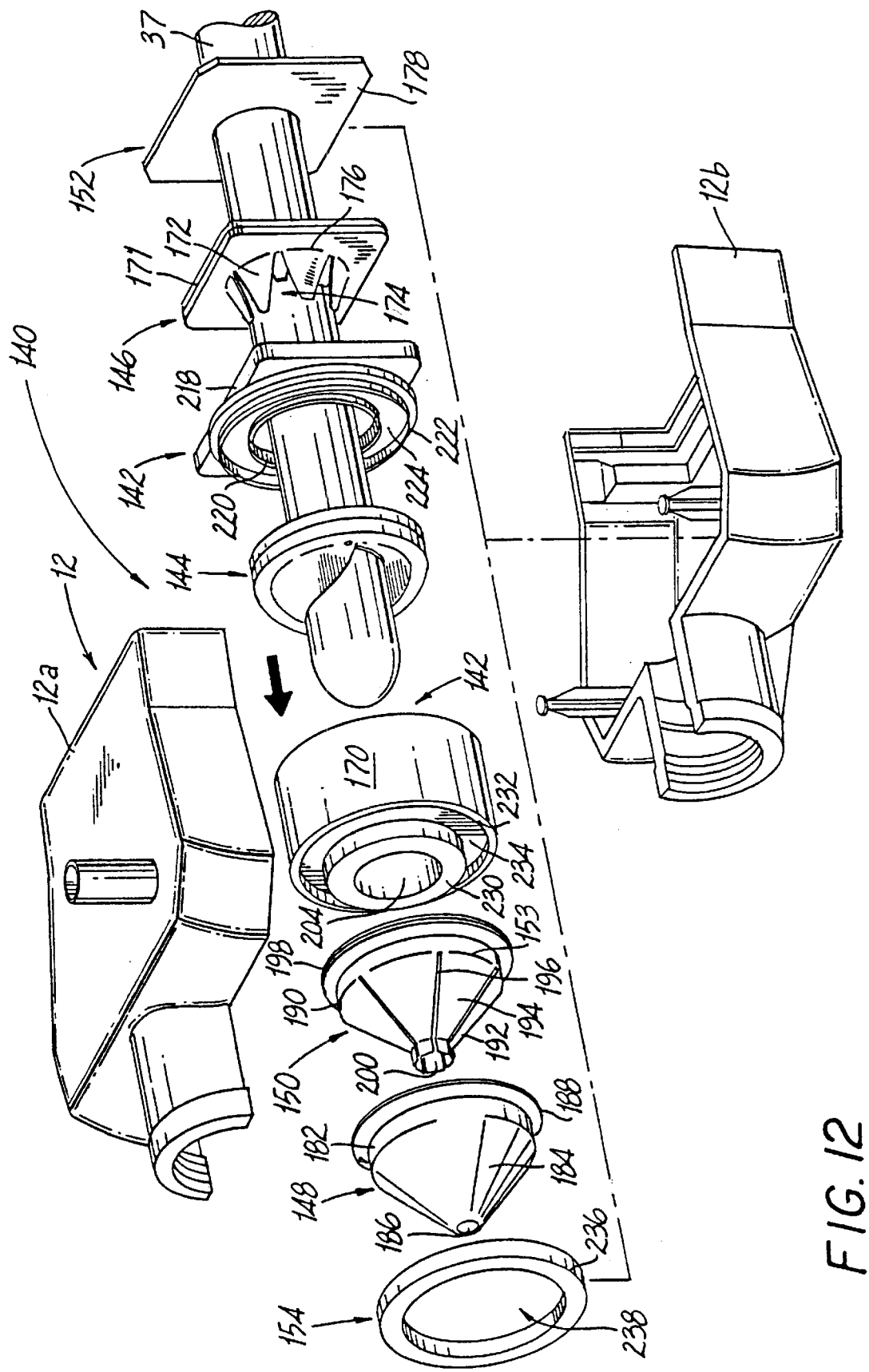
FIGS. 12, 13 and 14 are exploded perspective views of a cannula assembly illustrating the valve assembly of FIG. 10 during the insertion of an instrument.

The tension is created in the walls 162 of the sealing gasket 144 by stretching each element 156, 158 onto the pins 168 of the housing assembly 142. Each hole 166 mates with the corresponding pin 168 of the housing assembly 142. The pin 168 placement requires that the elements 156, 138 be substantially stretched to mate the holes 166 with the pins 168. This secures the elements to the cylindrical body portion of the housing assembly 142 while creating and maintaining the desired wall 162 tension. As shown in FIG. 12, flexible resilient walls accommodate an instrument 37 by resiliently deforming to enable the instrument 37 to pass therethrough. Fluid flow is discouraged around the instrument by the flexible elements 156, 158 substantially surrounding the instrument 37 as it is passed therethrough. The tensioning of the overlapping elements 156, 158 further provides radial tensioning of the overlapping elements 156, 158 on the surface of the instrument. The contact between the overlapping elements 156, 158 and the surface of the instrument helps to prevent the unwanted egress of fluids when an instrument 37 is passed through the valve assembly.

Upon removal of instrument 37, resiliently deformable sealing gasket assembly 144 returns to its initial position, thereby reestablishing a substantially fluid tight seal with the instrument 37 removed.

The valve assembly 140 may also include structure for inhibiting unwanted contact between an instrument being inserted and sealing structure, in this case, the sealing gasket assembly 144. A preferred embodiment of such structure is shown in FIGS. 10–14 as first and second square retainers 146. Although, the first and second retainers 146 are shown as square, other configurations are also contemplated, such as, circular. The retainers may be somewhat similar to the retainers 16 and 18 shown in FIG. 5 and described above.

Each of the square retainers 146 of the present embodiment shown in FIGS. 10–14 are essentially identical to each other and include a body portion 171 having a series of triangularly shaped portions 172 defining a series of slits 174 therebetween. As best seen in FIG. 11, preferably, a plurality of triangularly shaped movable portions 172 are divided by a series of slits 174 and are attached to the body portion 171 by hinge-like regions 176. The triangularly shaped portions 172 are positioned radially about a substantially central axis. The slits 174 of the one of the retainers 146 bisect the triangular portions 172 of the other retainer 146. The square retainers 146 are preferably formed of a suitable synthetic resin or plastic, such as polypropylene.

The square retainers 146 are juxtapositioned such that the slits of one of the retainers transect the triangular portions 172 of the other retainer to provide enhanced protection of the sealing gasket assembly 144 from an instrument inserted into the valve assembly 140.

As the instrument passes through the square retainers 146, the triangular portions 172 accommodate the instrument by moving distally exposing the slit 174 therebetween to the entering instrument. However, the adjacent sealing gasket assembly 144 remains uninjured by the entering instrument because the overlapping square retainers 146 distally positioned with respect to triangular portions 172 discourage the instrument from contacting the sealing gasket assembly 144. Contact is discouraged because the square retainers 146 are positioned between the entering instrument and the sealing gasket assembly 144, and the juxtapositioning of the square retainers 146 provide a substantially continuous surface protecting the sealing gasket assembly 144.

The valve assembly 140 may also include structure for stabilizing the instrument when the instrument is passed through the valve assembly 140. An embodiment of such structure in accordance with the present invention is shown in FIGS. 10–14 as a stabilizer plate positioned proximally of the square retainer plates 146.

The stabilizer plate 152 has some similarities to the stabilizer plate 64 shown in FIG. 5. The stabilizer plate 152 shown in FIGS. 10–14 is generally square in shape and includes a body portion 178 defining a substantially central circular aperture 180 therethrough to accommodate a surgical instrument. The stabilizer plate 64 provides rigidity to the overall valve assembly 140, and further guides an instrument through a desired passageway in the valve assembly 140.

The valve assembly 140 may also include sealing structure comprising a third sealing element for substantially sealing the valve assembly after an instrument is passed therethrough. An embodiment of such a third sealing element in accordance with the present invention is shown in FIGS. 10 and 12–14 as a conical seal 148 positioned distally adjacent to conical retainers 150 and constructed of a suitable flexible resilient material.

The conical seal 148 includes a body portion 182 having a tapered section 184 which has a substantially conical configuration and a substantially central hole 186 therethrough. The body portion 182 further includes a circumferential ridge 188 positioned proximal to the tapered section 184. The ridge 188 is substantially integral with the body portion 182 and extends radially outwardly from the body portion 182.

The conical seal 148 is preferably formed of an elastomeric material such as, for example, natural rubber.

Figure 14:
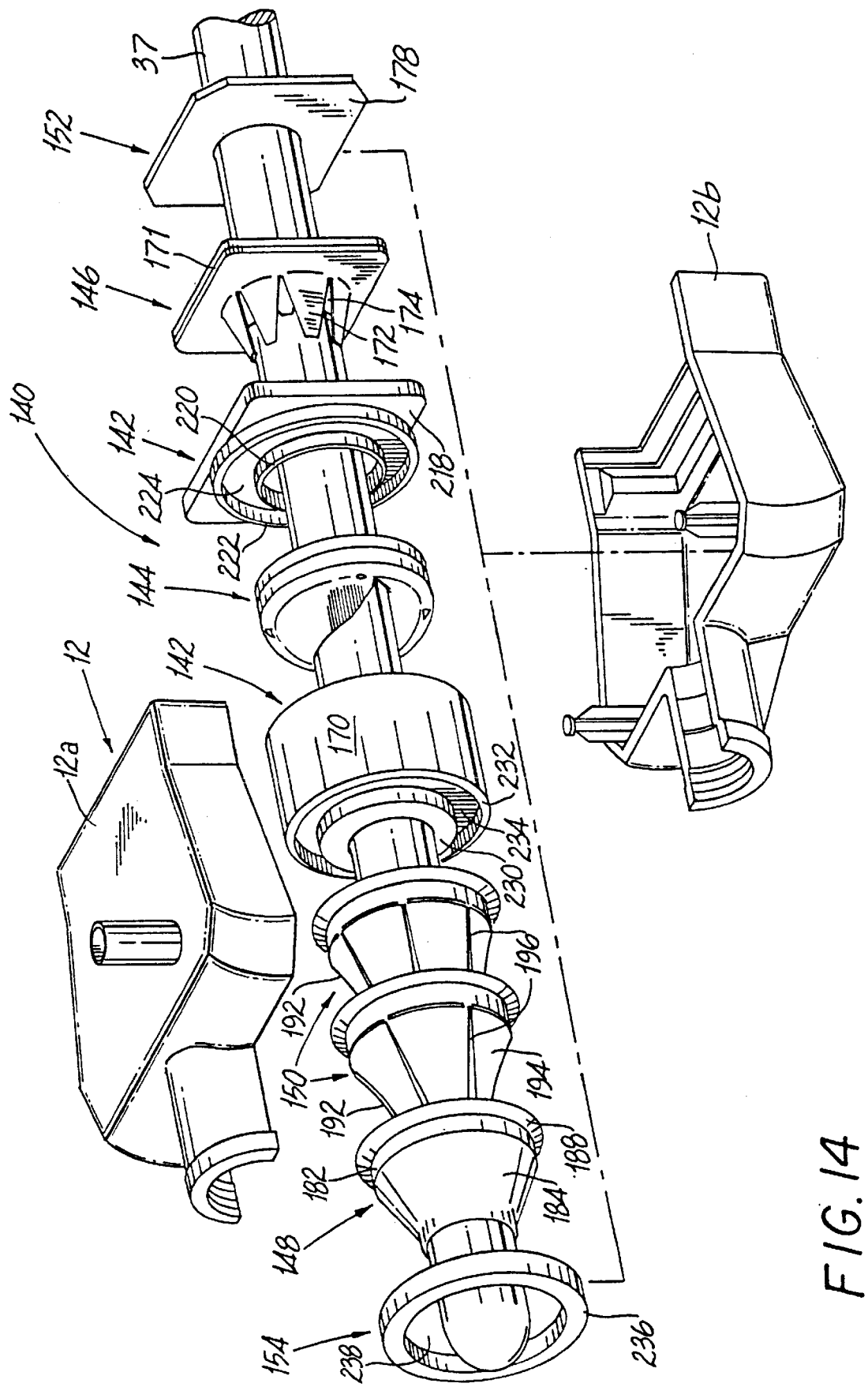

The elastomeric material of the conical seal 148 allows the conical seal 148 to accommodate instruments of varying diameters through its central aperture 186. The elastomeric tapered section 184 of the conical seal 148 deforms and flexes for sealing about the instrument passed therethrough. As the instrument is passed through the hole of the tapered section 184, the elastomeric material of the conical section deforms to accommodate the instrument, as shown in FIG. 14. The deformation of the tapered section 184 is desirable for substantially sealing about the instrument.

The flexible material of the tapered section 184 enables the hole 186 to accommodate instruments of varying sizes while providing a substantially fluid and gas tight seal about the instrument, e.g., instruments having diameters of from 3 mm to 15 mm. The size of the hole 186 in the conical seal 148 is typically less than 12 mm and preferably from 2.5 mm to 3.0 mm (0.10 inches to 0.12 inches). The material of the conical seal 148 preferably has a durometer value in the range of 30 to 45, and most preferably a durometer value of 40.

The conical configuration, or frustoconical shape of the conical seal 148 favorably influences the amount of insertion force required to pass an instrument therethrough. The conical shape of the seal 148 deformably adapts to the inserted instrument, thus, reduced insertion forces on the instrument are required.

The valve assembly 140 may also include another embodiment of a structure for inhibiting unwanted contact between an instrument being inserted and sealing structure, in this case, the conical seal 148. A preferred embodiment of such structure is shown in FIGS. 10, and 12–14, as conical retainers 150 which are essentially identical. Each conical retainer 150 includes a body portion 190 having a tapered portion 192 being generally conically shaped. The tapered portion 192 includes a series of triangularly shaped sections 194 defining a series of slits 196 therebetween. The triangularly shaped sections 194 are positioned radially about a substantially central axis. The slits 196 of one conical retainer 150 bisect the triangular sections 194 of the other conical retainer 150. The conical retainers 150 are preferably formed of a suitable synthetic resin or plastic, such as polypropylene.

As best seen in FIG. 12, preferably, a plurality of triangularly shaped movable portions 194 are divided by a series of slits 196 and are attached to the perimeter 198 of the conical retainers 150 by hinge regions 153. The slits 196 extend radially outward from central aperture 200 of the conical retainers 150. The conical retainers 150 are juxtapositioned such that the slits 196 of one of the retainers transect the triangular portions 194 of the other retainer, in a similar manner as with the square retainers 146.

When an instrument is passed through conical retainers 150, thereby entering the conical seal 148, the triangular portions 194 discourage unwanted contact with the conical seal 148. Contact is discouraged in a similar manner as with the square retainers 146 discussed above.

The housing assembly 142 of the valve assembly 140 shown in FIGS. 10–14 is a preferred embodiment of a structure for tensioning overlapping first and second elements of the sealing gasket assembly 144. The housing assembly 142 comprises a cylindrical body portion 170 having a passageway 204 therethrough. The cylindrical body portion 170 may act as a frame for receiving the sealing gasket assembly 144. The housing assembly 142 further includes a housing end cap 218 removably positioned proximal to the cylindrical body portion 170, and a fastening ring 154 positioned distal to the body portion 170. The proximal end of the cylindrical body portion 170 of the housing assembly 142, as best seen in FIG. 11 includes outer and inner ridges 210, 212, both extending proximally with respect to the cylindrical body portion 170. The ridges 210, 212 define a groove 214 therebetween that is dimensioned and configured for mating with the sealing gasket assembly 144. The ridge 210, 212 also includes a groove 216 circumscribing an inner surface of the outer ridge 210 which is also dimensioned and configured to receive the sealing gasket assembly 144.

Further, two pins 168 extend proximally from the cylindrical body portion 170. The two pins 168 are passed through the mating holes 166 in the sealing gasket assembly 144 to provide the desired tensioning of the gasket sealing assembly 144, as well as to fixedly position the sealing gasket 144 in the housing assembly 144.

The end cap 218 of the housing assembly 142 includes inner and outer 220, 222 concentric ridges defining a groove 224 therebetween. The groove 224 is dimensioned and configured to receive the proximal end of the sealing gasket assembly 144. Once the sealing gasket assembly 144 is seated therein, the housing end cap 218 can be mated with the cylindrical body portion 170 of the housing assembly 142. The housing end cap 218 and the cylindrical body porion 170 of the housing assembly 142 can be mated, for example, by welding, or adhesive, or by other methods known in the art.

As best seen in FIG. 11, the end cap 218 of the housing assembly 142 further includes a proximally extending rectangular portion 226. The rectangular portion 226 of the housing end cap 218 has a generally L-shaped inner portion having a proximally extending ridge 228. The inner side of the rectangular portion 226 is dimensioned and configured to removably receive the square retainers 146 and the stabilizer plate 152 providing positive placement of the retainers 146 and stabilizing plate 152 therein.

Figure 13:
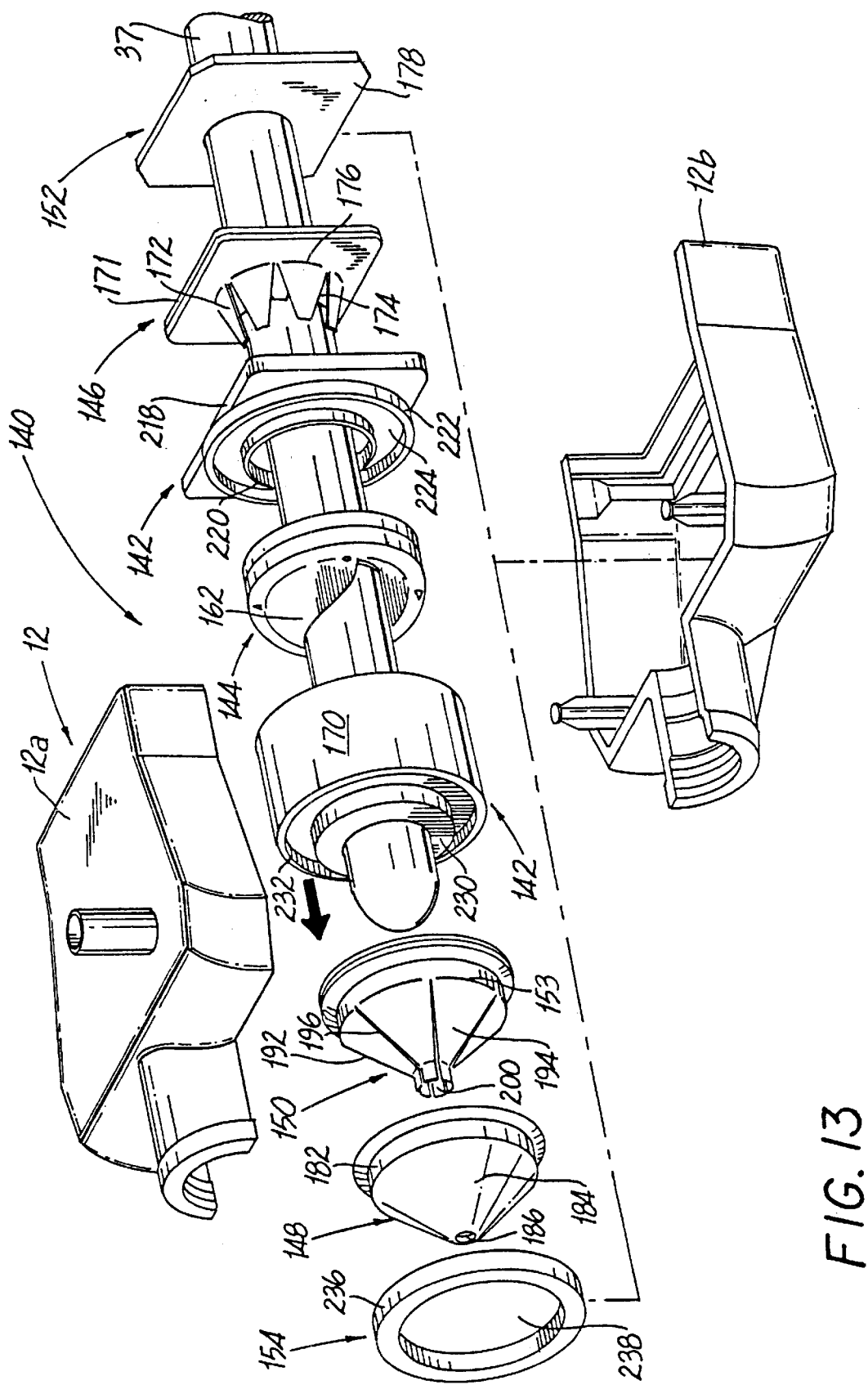

The cylindrical portion 170 of the housing assembly 142 further includes at its distal end, concentric inner and outer flanges 230 and 232 defining a channel 234 therebetween, as shown in FIGS. 12–14. The channel 234 is dimensioned and configured to accommodate the conical retainers 150, conical seal 148, and the fastening ring 154 in mating relation.

The fastening ring 154 is positioned distal to the conical seal 148. The fastening ring 154 includes a circular body portion 236 having an aperture 238 therethrough. The aperture 238 has an inner diameter dimensioned to fit over the tapered portion 184 of the conical seal 148 and abut ridge 188. The fastening ring 154 mates with the channel 234 to hold the conical seal 148 and the conical retainers 150 in place. The fastening ring 154 may be attached to the housing assembly 142 by, for example, welding or adhesive, or by other methods known in the art.

It is envisioned that the conical sealing member 148 and the sealing gasket assembly 144 can be positioned proximal or distal to each other and be equally effective.

Referring to FIGS. 10 and 17, according to the present invention, a tissue gripping apparatus 240 is used with the elongated tubularly shaped cannula 14. The tissue gripping apparatus 240 includes a cylindrical body portion 242, and a flexible element 246 having a plurality of substantially parallel articulated arms 248. Each of the arms 248 have a hinge 250 located proximal to a midpoint of each respective arm 248, preferably each hinge 250 is substantially the same distance from the midpoint of the respective arms 248.

The cylindrical body portion 242 may be constructed, preferably, of a substantially resilient flexible material such that the cylindrical body portion 242 can frictionally engage the elongated tubular cannula 14. The frictional engagement of the cylindrical body portion 242 with the cannula 14 allows the body portion 242 to be slidably positionable along the cannula 14. The body portion 242 is moved distally to fully deploy the tissue gripping apparatus 240; that is, when the articulated arms 248 are in an extended position bending at their hinges 250.

An actuation member 252 is situated at a proximal end of the cylindrical body portion 242. The actuation member 252 allows a surgeon to easily move the cylindrical body portion 242 distally to deploy the articulated arms 248. The articulated arms 248 are in a preferred deployed position when the arms 248 proximal the hinge 250 are in a substantially perpendicular orientation relative to the body portion 242. This perpendicular orientation ensures optimum retention of the surgical apparatus in, for example, the abdomen by securingly engaging the inner wall of the abdominal cavity. Other actuation systems whereby cylindrical body portion 242 may be moved distally to deploy arms 248 may, of course, be employed.

Referring to FIGS. 10 and 17, a cannula member 254 is provided for use with a tubular member, such as the cylindrical body portion 242 of the tissue gripping apparatus 240, or a cannula or similar device to deter the escape of gases from the body cavity passed the cannula inserted therein and to provide support to the cannula inserted in the body cavity. For example, gasses may escape when a surgeon is engaging in endoscopic or laparoscopic procedures requiring insufflation of the body cavity or the cannula may undesirably slant making instrument insertion difficult.

An embodiment of a cannula member 254 for use with a cannula 14 and working in concert with the tissue gripping apparatus 240 is shown in FIGS. 10 and 17. The illustrated cylindrical cannula member 254 is slidably positioned about the body portion 242 of the tissue gripping apparatus 240. The cannula member 254 includes a body portion 256 having concentric inner and outer flanges 258, 260. The flange 258 and 260 are positionable against a patient's body to provide sealing and stabilizing properties.

The cannula member may be, for example, constructed of an elastomeric material, which is preferably an elastomer commercially available under the trademark "SANTOPRENE", manufactured by Monsanto.

The cannula member 254 is contemplated to be rigid enough such that the flanges 258, 260 of the cannula member can be placed against a patients skin to enhance stabilization of the cannula 14 positioned through the body wall of the patient. The cannula's 14 increased stability provides greater ease of entry into the cannula 14 by the surgeon, as well as, moderating angular movement of the cannula 14. This increased stability decreases the likelihood of irritation or trauma around the entry site of the cannula 14 into the body cavity.

Although the cannula member moderates angular movement of the cannula 14, some angular movement of the cannula 14 is likely and may be desirable. Cannula member 254 is designed to remain in substantial contact with the patient's body while accommodating the cannula 14 in varying angular positions with respect to the patient's body.

In operation, the cannula member 254 as shown in FIGS. 10 and 17 is used with the cannula 14 and in concert with the tissue gripping apparatus 240. Typically, a trocar device including, for example, an obturator (not shown) and a cannula 14 is employed to puncture the skin and provide access to the surgical area. A pointed obturator may be used for penetrating the skin to extend the trocar beyond the body wall to the surgical site. Alternatively, an incision may be made using a scalpel or similar device before inserting a blunt obturator through the incision. When either obturator is removed, the cannula remains in place to maintain access to the surgical site, and several incisions may be made to provide numerous access ports to the surgical objective.

Once the cannula(s) are in place, the tissue gripping apparatus 240 is actuated into a deployed position by moving the actuation member 252 distally. The articulated parallel arms 248 move outwardly as hinges 250 extend the parallel arms 248 to a fully deployed position. The location of the hinge 250 on the articulated parallel arms 248 allows the portion of the arms 248 proximal the hinge 250 to be substantially perpendicular to the tubular portion 242 of the tissue gripping apparatus 240. The cannula 14 is thereby secured in the incision by the extended articulated parallel arms 248 of the tissue gripping apparatus 240.

The cannula member 254 is then urged towards the patient's body by manually advancing the cannula member 254 distally until the inner and outer flanges contact the patient's skin. The inner and outer flanges 258, 260 contact the patient's skin providing a substantial gas seal for maintaining insufflation pressure within the body cavity, and stabilizing the cannula 14 in the incision.

The cannula member 254 is designed to remain in substantial contact with a patient's body while accommodating the cannula 14 in varying angular positions with respect to a patient's body. More specifically, the cannula member 254 is at least partially constructed of flexible material which allows for angular juxtapositioning of the cannula 14 with respect to a patient's body while maintaining a substantial relationship between the flanges of the cannula member 254 and a patient's body.

The cannula member 254 has adequate rigidity for providing stabilization of the cannula 14. The rigid nature of the cannula member 254 enhances support of the cannula 14 positioned through an incision in the body cavity. The cannula's 14 increased stability provides greater ease of entry into the cannula 14 by the surgeon, as well as, moderating angular movement of the cannula 14. This increased stability decreases the likelihood of irritation or trauma around the entry cite of the cannula into the body cavity.

Referring to FIGS. 12–14, the valve assembly 140 operates as described below. A surgical instrument may be inserted at the proximal end of the cannula housing 12. As the instrument 37 is passed through the valve assembly 140, the stabilizer plate 152 receives the instrument 37 and guides the instrument 37 into the valve assembly 140, as shown in FIG. 12.

As an instrument 37 passes through the retainers 146 the triangular plates 172 pivot distally from a longitudinal center line of the retainers 146. The overlapping retainers 146 encourage the instrument through the valve assembly 140 by assisting the sealing gasket assembly 144 to accommodate the instrument 37. The triangular portions 172 of the retainers 146 displace the flexible resilient material of the adjacent sealing gasket assembly 144 encouraging easier access for the instrument 37.

Further, the triangular movable portions 172 of the retainers 146 discourage unwanted contact between the instrument 37, such as a trocar obturator having a sharp tip, and the sealing gasket assembly 144. More specifically, the retainers 146 provide an intermediate surface between a sharp instrument being inserted into the valve assembly 40 and the adjacent sealing gasket assembly 140. Both retainers also provide support to the valve assembly 140 such that manipulation of the instrument 37 will not deter the instrument from the desired passageway, or compromise the valve assembly's 140 sealing effect.

Further, the square retainers 146 are juxtapositioned such that the slits of one retainer 146 transect the triangular portions 172 of the other, as shown in FIG. 11. This overlapping arrangement more effectively discourages unwanted contact between the instrument 37 and the other members of the valve assembly, in this case the sealing gasket assembly 144.

Referring to FIG. 12, as the instrument 37 continues through the valve assembly 140 it enters the housing assembly 142 and engages the sealing gasket assembly 144. The sealing gasket assembly 144 accommodates the instrument 37 in the operable passageway defined by the overlapping elements 156, 158. The overlapping elements 156, 158 substantially surround the outer surface of the instrument 37 and discourage fluids and gasses from escaping from around the instrument 37.

Referring to FIGS. 13 and 14, as the instrument 37 extends through the distal end of the housing assembly 142, it engages the conical retainers 150 and the conical seal 148. As with the square retainer 146 described above, the triangular portions 194 of the conical retainers 150 discourage unwanted contact with the conical seal 148. Contact is discouraged because the conical retainers 150 are positioned between the entering instrument 37 and the conical seal 148.

Further, similarly to the square retainers 146 described above, as an instrument 37 passes through the conical retainers 150 the triangular plates 194 pivot distally from a longitudinal center line of the retainers 150. The overlapping retainers 150 encourage the instrument 37 through the conical seal 148 by assisting the conical seal 148 to accommodate the instrument 37. The triangular portions 194 of the retainers 150 displace the flexible resilient material of the adjacent conical seal 148 encouraging easier access for the instrument 37.

As the instrument 37 is passed through the central aperture 186 of the conical seal 148 the elastomeric material of the tapered section 184 deforms and flexes to accommodate the instrument 37. The flexible nature of the conical seal 148 provides sealing about the instrument 37 passed therethrough.

After the surgery is completed, the surgical instrument 37 may be withdrawn from the cannula 14. The valve assembly 140 provides substantial fluid and gas tight sealing before and after the instrument 37 is withdrawn.

To remove the cannula 14, the cannula member 254 may first be manually moved proximally, or the cannula member 254 may also be moved proximally by releasing the tissue gripping apparatus 240. By either method, the distal movement of the cannula member 254 removes the flanges 258, 260 from contact with the patient's skin.

The tissue gripping apparatus 240 may be removed by releasing the articulated parallel arms 248 of the tissue gripping apparatus 240. The articulated parallel 248 arms are returned to their at rest position by moving the actuation member 252 proximally.

After the tissue gripping apparatus 240 is released, the entire tissue gripping apparatus 240, and cannula 14 may be withdrawn from the incision.

Another embodiment of a valve assembly positioned in a cannula housing 12 is shown in FIGS. 15 and 16. The valve assembly 262 is essentially identical to the previous valve assembly 140 shown in FIGS. 10–14, however, the embodiment illustrated in FIGS. 15 and 16 includes sealing structure having a fourth sealing element embodied as wiper means or spitback seal 264. The similar elements between the embodiments shown in FIGS. 10–14 and FIGS. 15 and 16 function in a similar manner to the valve assembly 140 embodiment shown in FIGS. 10–14 and described above. However, the spitback seal 264 of the embodiment shown in FIGS. 15 and 16 includes characteristics as described below.

The spitback seal 264 is preferably positioned between a end cap 218 of housing Assembly 142 and a stabilizing plate 152. The spitback seal 264 may also be positioned at other locations, such as, distal to the sealing gasket assembly 144.

Typically, as the instrument 37 is removed from the valve assembly 262, fluids may be on the surface of the instrument and are removed with the instrument 37. These unwanted fluids can be disruptive to the surgeon. To substantially discourage such fluids from egressing from the valve assembly 262 in this manner, a spitback seal 264 is provided.

The spitback seal 264, preferably, has a generally square shape, but may be other configurations, such as rectangular.

The spitback seal 264 is constructed at least partially of a deformable material defining a substantially central aperture 266. The substantially central aperture accommodates the instrument 37, as seen in FIG. 16, such that the deformable material defining the aperture 266 contacts the outer surface of the instrument 37 substantially removing fluids therefrom.

More specifically, as the instrument 37 is withdrawn from the valve assembly 262, the deformable material of the spitback seal 264 which defines the aperture 266 therethrough substantially engages the outer surface of the instrument 37. The flexible nature of the spitback seal 264 may deform in a proximal direction as shown in FIG. 16. This deformability substantially enables the material of the spitback seal 264 defining the aperture 266 to remove fluids clinging to the surface of the instrument 37 as the instrument 37 is removed from the valve assembly 262. Thus, fluids are discouraged from exiting the valve assembly 262 as the instrument 37 is removed therefrom.

Another embodiment of a valve assembly 270 positioned in a cannula housing 12 is shown in FIGS. 17–20. The valve assembly 270 may include similarities to the previous valve assembly 140 shown in FIGS. 10–14.

Referring to FIG. 17, the valve assembly 270 includes stabilizer plate 152, square retainers 146, sealing gasket assembly 144, and housing assembly 142, which are essentially identical to those shown in FIGS. 10–14 as part of valve assembly 140 described above.

The valve assembly 270 further includes first and second circular retainers 272 which are essentially identical. Each retainer 272 includes a body portion 274 having a plurality of movable triangular portions 276 movably attached to the body portion 274. In both circular retainers 272 the plurality of triangular portions 276 are divided by a series of slits 278. The slits 278 extend radially from a substantially central aperture 280. The circular retainers 272 are juxtapositioned such that the slits 278 of one of the retainers 272 transect the triangular portions 276 of the other retainer 272.

The valve assembly 270 further includes sealing structure comprising a fifth sealing element embodied as a bellows seal 20 for substantially sealing the valve assembly after an instrument is passed therethrough. The bellows seal 20 is identical to the bellows seal 20 shown in FIGS. 1 and 5. The bellows seal 20, shown in FIGS. 17–20 is positioned distal to the retainers 272. The bellows seal 20 mates with the circular retainer 272 in a similar manner as the bellows seal 20 mates with the second rectangular retainer 18 and second circular retainer 116 shown in FIG. 5.

The bellows seal 20 and the circular retainers 272 are positioned in the channel 234 of the housing 142 in a similar manner as with the conical seal 148 and conical retainers 150 shown in FIGS. 10–14. Further the fastening ring 154 secures the bellows seal 20 and the circular retainers 272 in the housing assembly 142 in a similar manner as with the conical seal 148 and conical retainers 150 shown in FIGS. 10–14.

Figure 18:
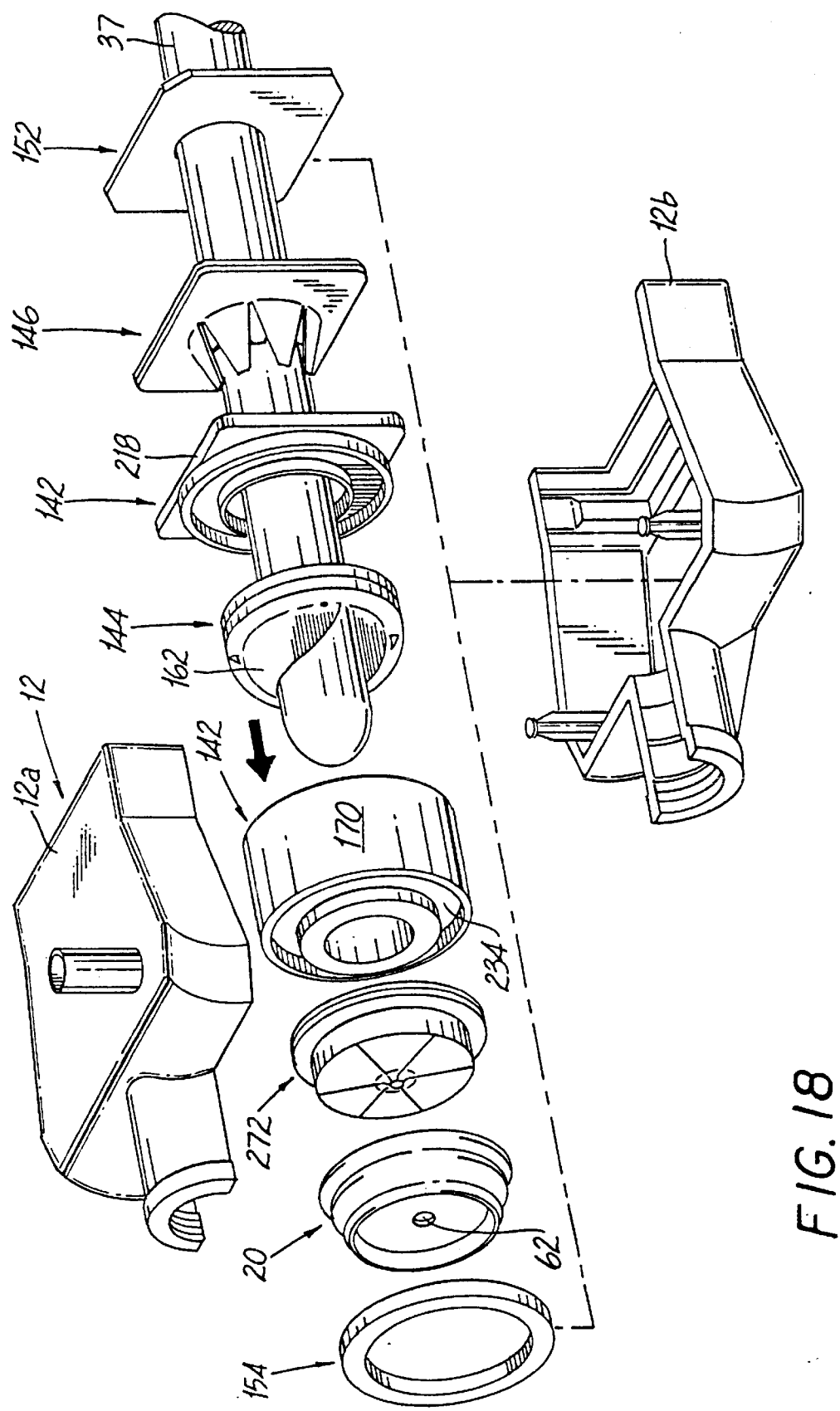
FIGS. 18, 19 and 20 are exploded perspective views illustrating the cannula and valve assembly of FIG. 17 during the insertion of an instrument.
Figure 19:
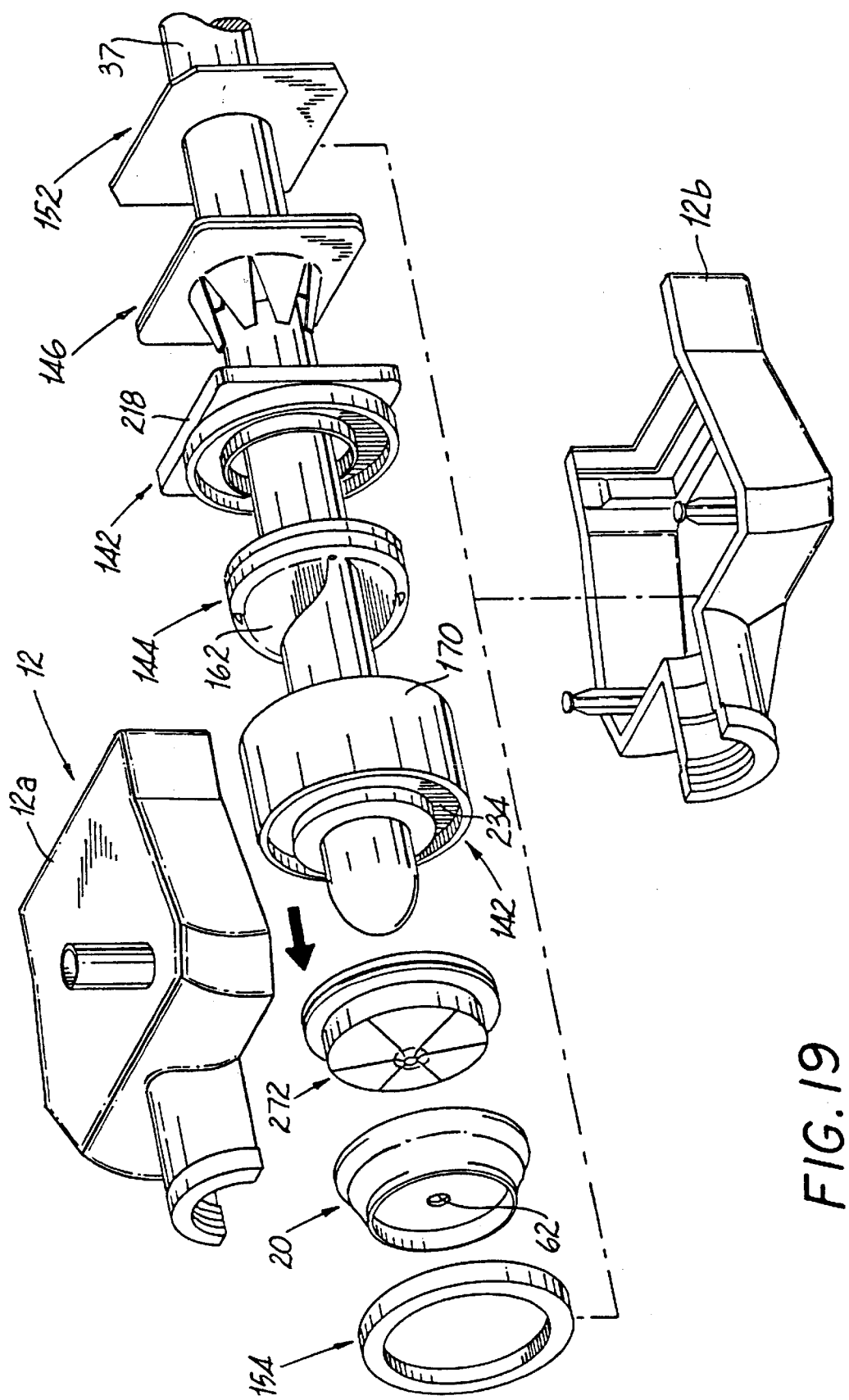

In operation, referring to FIGS. 18 and 19, as an instrument passes through the square retainers 146, and the gasket seal 144 housed in the housing assembly 142, the retainers 146 and the gasket seal 144 accommodate the instrument 37 in essentially the same manner as in valve assembly 140 described above and shown in FIGS. 10–14.

Figure 20:
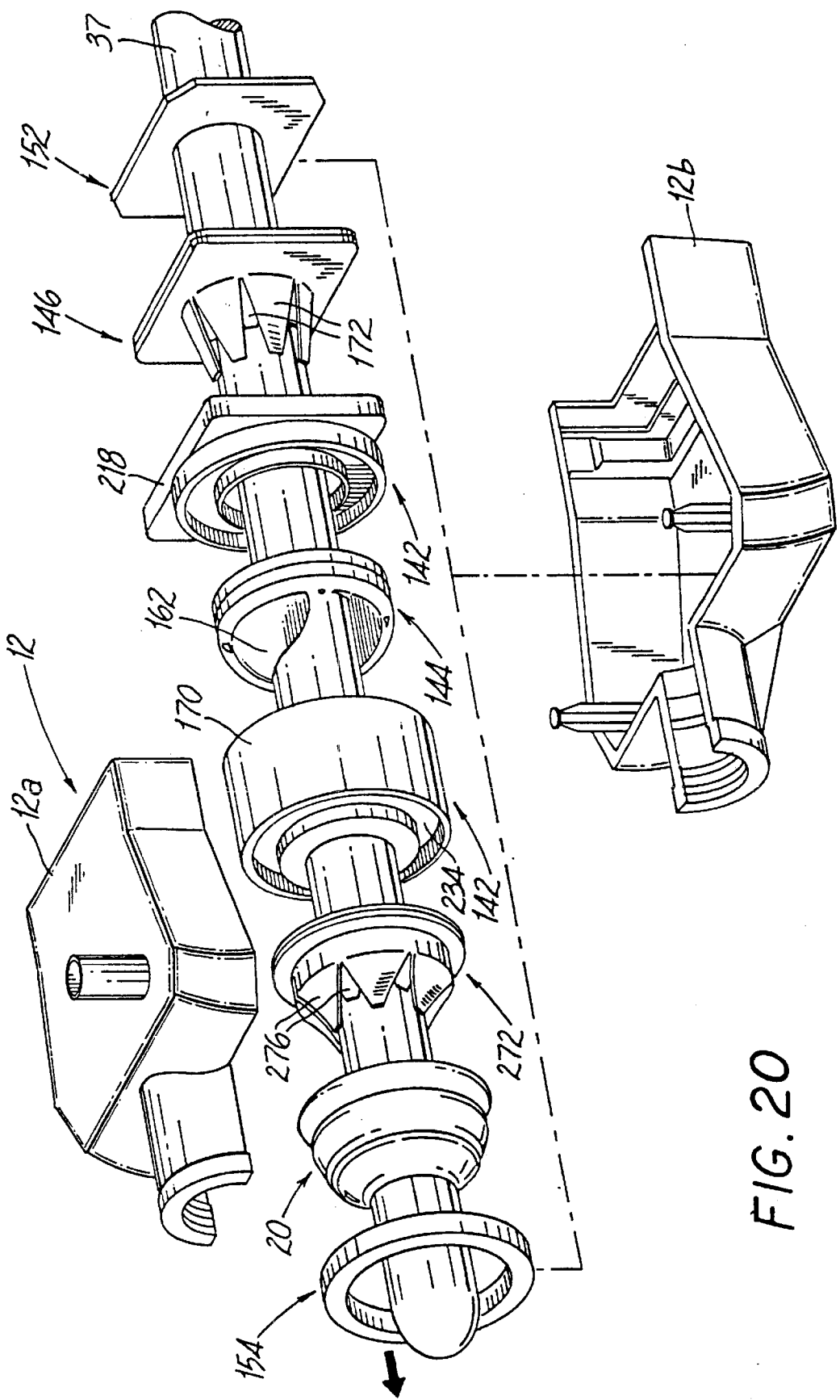

Referring to FIG. 20, the instrument engages the first and second circular retainers 272 and the bellows seal 20 in a manner which may be similar to the retainers 18, and 116 and the bellows seal 20 shown in FIG. 5. As shown in FIG.

20, the overlapping circular retainers 272 encourage the instrument 37 through the valve assembly 270 by assisting the bellows seal 20 to accommodate the instrument 37. Further, the triangular movable portions 172, 276 of the 254 circular retainers 146, 272 discourage unwanted contact between the instrument 37 and the sealing gasket assembly 144 and the bellows seal 20.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A seal assembly which comprises:
   (a) a frame;
   (b) at least one sealing gasket assembly constructed of a flexible material and mounted to said frame, the sealing gasket assembly including:
      (i) a first sealing element defining a first semi-circular opening and having a first wall, and
      (ii) a second sealing element defining a second semi-circular opening and having a second wall; and
   (c) at least one retainer element defining a substantially central aperture, said retainer element including a body portion and a plurality of adjacent movable portions joined to said body portion by hinge regions said adjacent movable portions being configured and dimensioned to inhibit contact between an instrument and said at least one sealing gasket assembly upon insertion of the instrument through the sealing gasket assembly, wherein said adjacent movable portions are each defined by a pair of slits extending radially at least partially between said adjacent movable portions from said substantially central aperture;
      wherein mounting of the at least one sealing gasket assembly onto the frame tensions the first and second walls so that they overlap to define overlapping walls and form a substantial gas and fluid tight seal in the absence of the instrument inserted through the semi-circular openings; and
      further wherein the overlapping walls are separable so, as to allow passage of the instrument through the semi-circular openings.

2. A seal assembly according to claim 1 wherein said frame includes at least two attachment members to engage and tension said first and second walls.

3. A seal assembly according to claim 1 wherein the frame tensions the first and second walls by resiliently stretching the overlapping walls.

4. A seal assembly according to claim 1 wherein said at least one sealing gasket assembly is constructed from a flexible material having a durometer value between 25 and 35.

5. A seal assembly according to claim 1 further comprising a housing structure which surrounds and encloses said frame.

6. A seal assembly according to claim 1 wherein at least one of said plurality of movable portions pivots distally from a substantially central longitudinal axis of said seal assembly.

7. A seal assembly according to claim 1, wherein a force is required to insert the instrument having a diameter of no more than about 15 mm through said semi-circular openings of said at least one sealing gasket assembly and said force is no more than about 7 pounds.

8. A seal assembly according to claim 1, wherein the plurality of movable portions are disposed along a plane in the absence of the instrument being inserted therethrough.

9. A seal assembly according to claim 1, which further comprises a plurality of retainer elements, each of said plurality of retainer elements defining a substantially central aperture, and including a plurality of adjacent movable portions configured and dimensioned to inhibit contact between the instrument and said at least one sealing gasket assembly upon insertion of the instrument through the sealing gasket assembly, wherein said adjacent movable portions are each defined by a pair of slits extending radially at least partially between said adjacent movable portions from said substantially central aperture.

10. A seal assembly according claim 9, wherein the plurality of retainer elements comprises two retainer elements which are juxtapositioned relative each other.

11. A seal assembly according to claim 10, wherein said two retainer elements are positioned relative each other such that said II plurality of movable portions of one of said two retainer elements are axially offset relative to the plurality of movable portions of the other of said two retainer elements.

12. A seal assembly according to claim 1, wherein said plurality of movable portions are formed of plastic.

13. A seal assembly according to claim 1 further comprising a plurality of retainer elements, each of said plurality of retainer elements defining a substantially central aperture, and including a plurality of adjacent movable portions configured and dimensioned to inhibit contact between the instrument and said at least one sealing gasket assembly upon insertion of the instrument through the sealing gasket assembly, wherein said adjacent movable portions are each defined by a pair of slits extending radially at least partially between said adjacent movable portions from said substantially central aperture, said plurality of retainers being positioned such that said plurality of adjacent movable portions of a first of said plurality of retainer elements are in overlapping juxtaposed relation with said plurality of adjacent movable portions of a second of said plurality of retainer elements.

14. A seal assembly according to claim 13 wherein each of said plurality of adjacent movable portions of said plurality of retainer elements is triangular-shaped, and further wherein at least one of said slits which defines a triangular-shaped movable portion of said first retainer element transects the triangular-shaped movable portion of another of said second retainer element.

* * * * *